United States Patent
Gravett et al.

(10) Patent No.: US 9,492,383 B2
(45) Date of Patent: Nov. 15, 2016

(54) RAPID IN-SITU GEL FORMING COMPOSITIONS PREPARED VIA REACTION OF VINYL SULFONE DERIVATIZED HYALURONIC ACID WITH THIOL DERIVATIZED POLYETHYLENE GLYCOL AT ALKALINE PH

(75) Inventors: David M. Gravett, Mountain View, CA (US); George Y. Daniloff, Los Altos, CA (US); Pingren He, Sunnyvale, CA (US)

(73) Assignee: Carbylan Therapeutics, Inc., Newark, CA (US)

(*) Notice: Subject to any disclaimer, the term of this patent is extended or adjusted under 35 U.S.C. 154(b) by 0 days.

(21) Appl. No.: 14/112,234

(22) PCT Filed: Apr. 18, 2012

(86) PCT No.: PCT/US2012/034133
§ 371 (c)(1),
(2), (4) Date: Oct. 16, 2013

(87) PCT Pub. No.: WO2012/145439
PCT Pub. Date: Oct. 23, 2012

(65) Prior Publication Data
US 2014/0221307 A1    Aug. 7, 2014

Related U.S. Application Data

(60) Provisional application No. 61/477,563, filed on Apr. 20, 2011.

(51) Int. Cl.
| | | |
|---|---|---|
| *A61K 9/06* | (2006.01) |
| *A61K 31/765* | (2006.01) |
| *A61L 26/00* | (2006.01) |
| *A61L 27/20* | (2006.01) |
| *A61L 27/52* | (2006.01) |
| *A61L 27/18* | (2006.01) |
| *A61L 27/54* | (2006.01) |
| *A61L 31/04* | (2006.01) |
| *A61L 31/06* | (2006.01) |
| *A61L 31/14* | (2006.01) |
| *A61L 31/16* | (2006.01) |
| *A61K 31/728* | (2006.01) |
| *A61K 45/06* | (2006.01) |

(52) U.S. Cl.
CPC ............. *A61K 9/06* (2013.01); *A61K 31/728* (2013.01); *A61K 31/765* (2013.01); *A61K 45/06* (2013.01); *A61L 26/008* (2013.01); *A61L 26/0019* (2013.01); *A61L 26/0023* (2013.01); *A61L 27/18* (2013.01); *A61L 27/20* (2013.01); *A61L 27/52* (2013.01); *A61L 27/54* (2013.01); *A61L 31/042* (2013.01); *A61L 31/06* (2013.01); *A61L 31/145* (2013.01); *A61L 31/16* (2013.01); *A61L 2300/222* (2013.01)

(58) Field of Classification Search
None
See application file for complete search history.

(56) References Cited

U.S. PATENT DOCUMENTS

| | | | |
|---|---|---|---|
| 4,582,865 A | 4/1986 | Balazs et al. | |
| 7,196,180 B2 | 3/2007 | Aeschlimann et al. | |
| 7,829,118 B1 | 11/2010 | Gravett et al. | |
| 8,790,702 B2 * | 7/2014 | Gravett et al. | 424/488 |
| 2010/0144902 A1 * | 6/2010 | Shu | 514/774 |

FOREIGN PATENT DOCUMENTS

| | | |
|---|---|---|
| EP | 2177236 A1 | 4/2010 |
| WO | 2006/056204 A1 | 6/2006 |
| WO | 2011/014432 A1 | 2/2011 |
| WO | 2011/031402 A1 | 3/2011 |

OTHER PUBLICATIONS

Allison and Grande-Allen, "Review. Hyaluronan: a powerful tissue engineering tool", Tissue Engineering, vol. 12, No. 8, pp. 2131-2140 (2006).
International Search Report from related PCT Patent Application No. PCT/US2012/034133 mailed on Jun. 27, 2012, application now published as PCT Patent Publication No. WO2012/145439 on Oct. 26, 2012.
Jin et al., "Synthesis and characterization of hyaluronic acid-poly(ethylene glycol) hydrogels via Michael addition: An injectable biomaterial for cartilage repair", Acta Biomaterialia, vol. 6, No. 6, 1968-1977 (2010).
Duflo et al., "Vocal fold tissue repair in vivo using a synthetic extracellular matrix", Tissue Engineering, vol. 12, No. 8, pp. 2171-2180 (2006).
Liu et al., "Osteochondral defect repair with autologous bone marrow-derived mesenchymal stem cells in an injectable, in situ, cross-linked synthetic extracellular matrix", Tissue Engineering, vol. 12, No. 12, pp. 3405-3416 (2006).
Stern, "Hyaluronan catabolism: a new metabolic pathway", Eur. J. Cell Biol., vol. 83, No. 7, pp. 317-325 (2004).
Hiemstra et al., "Novel in situ forming, degradable dextran hydrogels by Michael addition chemistry: Synthesis, rheology, and degradation", Macromolecules, vol. 40, pp. 1165-1173 (2007).
Qiu et al., "A hydrogel prepared by in situ cross-linking of a thiol-containing poly(ethyl glycol)-based copolymer: A new biomaterial for protein drug delivery", Biomaterials, vol. 24, pp. 11-18 (2003).
Schante et al., "Chemical modifications of hyaluronic acid for the synthesis of derivatives for a broad range of biomedical applications", Carbohydrate Polymers, vol. 85, pp. 469-489 (2011).
Van Tomme et al., "In situ gelling hydrogels for pharmaceutical and biomedical applications", Int. J. Pharm., vol. 355, No. 1-2, pp. 1-18 (2008).

* cited by examiner

*Primary Examiner* — Eric Olson
*Assistant Examiner* — Dale R Miller
(74) *Attorney, Agent, or Firm* — Susan T. Evans; McDermott Will & Emery LLP

(57) ABSTRACT

The present application provides rapid-gelling, sprayable hyaluronic-acid based compositions, kits, related methods, precursor formulations, and uses thereof.

30 Claims, 3 Drawing Sheets

RAPID IN-SITU GEL FORMING COMPOSITIONS PREPARED VIA REACTION OF VINYL SULFONE DERIVATIZED HYALURONIC ACID WITH THIOL DERIVATIZED POLYETHYLENE GLYCOL AT ALKALINE PH

CROSS-REFERENCE TO RELATED APPLICATIONS

This application is a U.S. National Stage of International Patent Application No. PCT/US2012/034133, filed Apr. 18, 2012, which claims the benefit of priority to U.S. Provisional Patent Application No. 61/477,563, filed Apr. 20, 2011, the contents each of which is incorporated herein by reference in its entirety.

FIELD

The disclosure relates generally to in-situ, gel-forming compositions, related kits, and methods of preparing and using such compositions, among other things. The in-situ gel forming compositions are generally prepared by mixing an aqueous solution of vinyl-sulfone-functionalized hyaluronic acid, a thiol-functionalized polyethylene glycol, and a buffer, under conditions suitable to form a gel within from seconds to an hour of mixing. The resulting biocompatible compositions can be used, for example, as biomedical adhesives and sealants, for localized delivery of bioactive agents, as bulking agents and fillers, among other uses.

BACKGROUND

Hyaluronic acid is a naturally-occurring, anionic, non-sulfated glycosaminoglycan that is distributed widely throughout connective, epithelial, and neural tissues. The average 70 kg (154 lbs) person possesses roughly 15 grams of hyaluronic acid in his/her body, one-third of which is turned over (degraded and synthesised) every day (Stern R. Eur J Cell Biol 83 (7): 317-25, (2004)). Since hyaluronic acid is found naturally in many tissues of the body and is therefore biocompatible, it is believed to be well suited for biomedical applications. Unfortunately, hyaluronic acid, when administered and used as a therapeutic in its naturally occurring form, is typically rapidly cleared from the body, making frequent administration necessary. Thus, formulations of hyaluronic acid which maintain the benefits of unaltered hyaluronic acid such as good biocompatibility, but which overcome the problem of rapid clearance are highly desirable. Such formulations should ideally have good cytocompatibility, beneficial chemical, rheological and other properties, and possess an ease of administration.

Modified forms of hyaluronic acid have been previously described. For example, hyaluronic acid having a low degree of substitution, as well as its lightly crosslinked products are described in International Patent Publication No. WO 2011/014432. The hydrogels and compositions described therein possess very low proinflammatory properties, along with several other advantageous features, but do not tend to undergo rapid gelation.

Rapid gelation is a general characteristic of in-situ forming gels. In-situ forming hydrogels are compositions that are liquid upon formation and application to a treatment site, but which undergo a phase transition to form a hydrogel thereafter. Biodegradable, injectable in-situ forming gels represent an attractive alternative to hydrogels provided as such, due to ease of administration and versatility in terms of gelation times, good adhesion, and the like.

Thus, it would be highly advantageous to form a composition possessing the advantages of the hydrogels described in International Patent Publication No. WO 2011/014432, but with the added and highly desirable benefit of being in the form of an in-situ forming gel.

SUMMARY

Provided herein are materials for preparing a liquid hydrogel precursor composition effective to form a hydrogel in-situ. The reactive precursor materials are sufficiently mild such that a liquid to solid phase transition can be carried out in situ, for example in direct contact with a tissue, in the absence of conditions or reactants that might otherwise be harmful to the tissue at the site where the gel forms. The resulting hydrogels possess good mechanical strength and can be prepared to have varying gelation times.

In a first general aspect, provided herein is a kit comprising components, which, upon mixing and application to a treatment site, results in hydrogel formation in-situ.

Generally, the kit comprises (i) a first container comprising an aqueous solution of vinyl sulfone-derivatized hyaluronic acid ("HA-VS") at a concentration of from about 10-300 mg/mL, where the VS-HS has from about 2%-70% of its hydroxyl groups substituted with vinyl sulfone, (ii) a second container comprising a thiol-functionalized polyethylene glycol having from 2 to 8 thiol groups, and (iii) a third container comprising a 30-1000 mM buffer solution at a pH ranging from about 7-12 to provide a solution having a HA-VS concentration of 2-8% (w/v) and a thiol-functionalized polyethylene glycol concentration of 2-8% (w/v), where the components, when combined, are effective to form a gel within seconds (e.g. 5 seconds) to 1 hour of mixing.

In yet another aspect, provided herein is liquid composition resulting from the combination of (i) an aqueous solution of vinyl sulfone-derivatized hyaluronic acid ("HA-VS") at a concentration of from about 10-300 mg/mL, where the VS-HS has from about 2%-70% of its hydroxyl groups substituted with vinyl sulfone, (ii) a thiol-functionalized polyethylene glycol having from 2 to 8 thiol groups, and (iii) a 30-1000 mM buffer solution at a pH ranging from about 7-12, where the concentration of the thiol-functionalized polyethylene glycol in the liquid composition ranges from about 4-300 mg/mL, or from 10-300 mg/mL, effective to form a gel within from seconds (e.g., 5 seconds) to about 1 hour of mixing.

In yet a further aspect, provided herein is a method of forming a liquid composition capable of in-situ gel formation. The method comprises: (i) adding a thiol-functionalized polyethylene glycol having from 2 to 8 thiol groups, preferably in powder form, to an aqueous solution of vinyl sulfone-derivatized hyaluronic acid ("HA-VS") having a concentration of from about 10-300 mg/mL, where the HA-VS has from about 2%-70% of its hydroxyl groups substituted with vinyl sulfone, to thereby dissolve the thiol-functionalized polyethylene glycol to form a vinyl sulfone-derivatized hyaluronic acid-thiol-functionalized polyethylene glycol-containing solution, and (ii) combining the solution from step (i) with a 30-1000 mM buffer solution at a pH ranging from about 7-12, to thereby form a liquid composition having a HA-VS concentration of 2-8% (w/v) and a thiol-functionalized polyethylene glycol concentration of 2-8% (w/v), wherein the liquid composition is effective to form a gel within from seconds to about 1 hour of combining.

In yet a further aspect, provided herein is an alternative method of forming a liquid composition capable of in-situ gel formation. The method comprises: (i) adding a small portion of thiol-functionalized polyethylene glycol, e.g., from about 0.1 wt % to about 4 wt % (wt/wt thiol-functionalized PEG to HA-VS), preferably in powder form, to an aqueous solution of vinyl sulfone-derivatized hyaluronic acid ("HA-VS") having a concentration of from about 10-300 mg/mL, where the VS-HS has from about 2%-70% of its hydroxyl groups substituted with vinyl sulfone, to thereby form a solution, (ii) optionally sterilizing the solution from step (i), (iii) adding to the solution from step (i) or step (ii) if conducted, to the remaining amount of thiol-functionalized polyethylene glycol, preferably in powder form, where the thiol-functionalized polyethylene glycol has from 2 to 8 thiol groups, and the thiol-functionalized polyethylene glycol is optionally sterile, to thereby dissolve the remaining amount of thiol-functionalized polyethylene glycol powder to form a vinyl sulfone-derivatized hyaluronic acid-thiol-functionalized polyethylene glycol-containing solution, and (iv) mixing the vinyl sulfone-derivatized hyaluronic acid-thiol-functionalized polyethylene glycol-containing solution with a 30-1000 mM buffer solution at a pH ranging from about 7-12, to thereby form a liquid composition having a HA-VS concentration of 2-8% (w/v) and a thiol-functionalized polyethylene glycol concentration of 2-8% (w/v), to thereby form a liquid composition effective to form a gel within from about seconds to about 1 hour of mixing.

In the aspects described above and related embodiments, any one or more of the aqueous solution of vinyl sulfone-derivatized hyaluronic acid ("HA-VS"), the thiol-functionalized polyethylene glycol, or the buffer solution, may be sterile.

Also provided herein are in-situ formed hydrogels resulting from the kits, the liquid composition, and the above-described methods, methods of application to a treatment site, methods of use, and the like.

Additional embodiments of the compositions, methods, kits, uses and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description, particularly when considered in conjunction with the accompanying examples and drawings.

DETAILED DESCRIPTION

Figure 1:
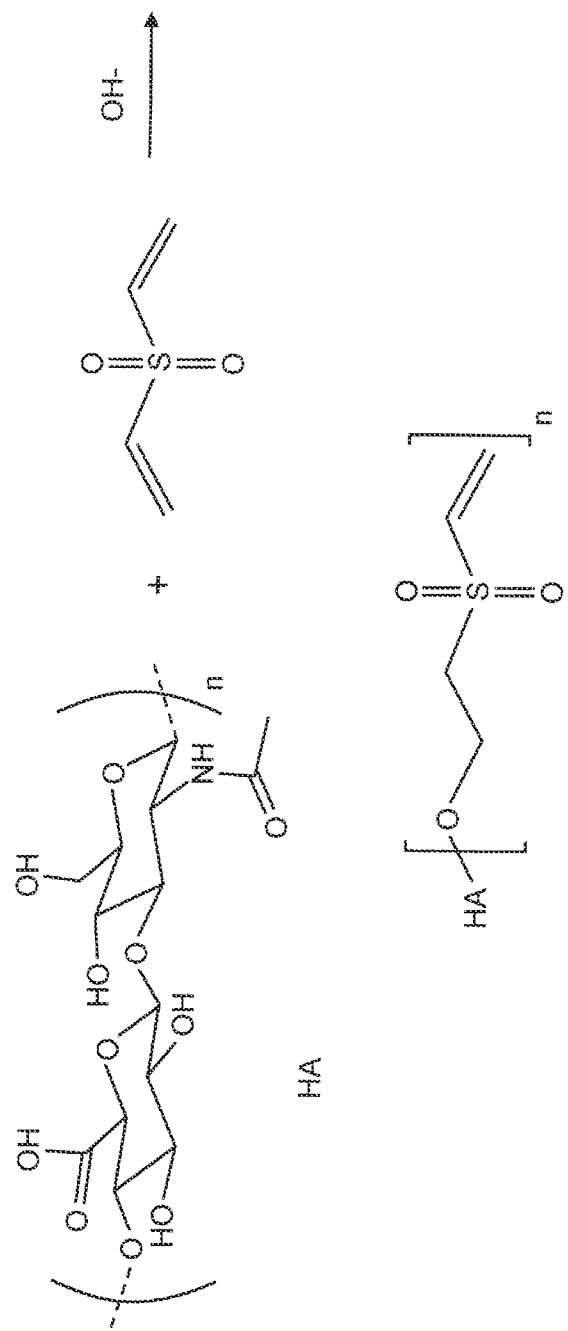
FIG. 1 shows the reaction of hyaluronic acid with divinyl sulfone in the presence of base to form vinyl-sulfone derivatized hyaluronic acid (HA-VS).

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

All publications, patents and patent applications cited herein, whether supra or infra, are hereby incorporated by reference in their entirety, unless otherwise indicated. In an instance in which the same term is defined both in a publication, patent, or patent application incorporated herein by reference and in the present disclosure, the definition in the present disclosure represents the controlling definition. For publications, patents, and patent applications referenced for their description of a particular type of compound, chemistry, etc., portions pertaining to such compounds, chemistry, etc. are those portions of the document which are incorporated herein by reference.

DEFINITIONS

It must be noted that, as used in this specification, the singular forms "a," "an," and "the" include plural referents unless the context clearly dictates otherwise. Thus, for example, reference to a "polymer" includes a single polymer as well as two or more of the same or different polymers.

Unless specifically noted otherwise, definitions of the terms herein are standard definitions used in the arts of organic synthesis, and polymer and pharmaceutical science.

In describing and claiming the present invention, the following terminology will be used in accordance with the definitions described below.

A "biocompatible polymer" is a polymer having degradation products that are compatible with living tissue, or that may have beneficial biological properties. The biocompatible polymer may be biocompatible in itself, and/or may be synergistically biocompatible when employed in conjunction with a biologically active agent.

The term, "hyaluronic acid", is meant to refer to unmodified or non-derivatized hyaluronic acid.

The terms "hyaluronic acid derivative" or "derivatized hyaluronic acid" or "modified hyaluronic acid" or "substituted hyaluronic acid" refers to hyaluronic acid that has been derivatized by reaction with, e.g., one or more small chemical moieties such as divinyl sulfone or the like.

The term "reactive" refers to a functional group (e.g., present in a polymer) that reacts readily or at a practical rate under conventional conditions of organic synthesis. This is in contrast to those groups that either do not react or require strong catalysts or impractical reaction conditions in order to react (i.e., a "nonreactive" or "inert" group).

"Molecular mass" or molecular weight, as used herein, in the context of a water-soluble polymer such as hyaluronic acid, refers to the nominal average molecular mass of a polymer determined by multi angle light scattering. Molecular weight can be expressed as either a number-average molecular weight or a weight-average molecular weight. Unless otherwise indicated, all references to molecular weight herein refer to the number-average molecular weight. In the absence of a molecular weight value, a polymer may also be characterized by its intrinsic or inherent viscosity, which is a viscometric method for measuring molecular weight.

The term "hydrogel" refers to a water-containing three dimensional hydrophilic polymer network or gel in which the water is the continuous phase, for example, in which the water content is greater than 50% (w/w).

The term, "spray" as used herein refers to an atomized composition.

By "gelation" is meant the formation of a material into a gelled state.

A "sterile" composition is one that is free of viable microbes as determined using the USP sterility test. See "The United States Pharmacopeia", 30th Revision, The United States Pharmacopeial Convention: 2008.

The term "sponge" as used herein means a porous hydrogel structure.

The phrase "soluble in aqueous solution" refers to a composition or compound that is capable of dissolving in aqueous buffer such as phosphate buffered saline at a concentration of at least 0.1 mg/mL at room temperature.

The term "drug," or "pharmaceutically active agent" or "bioactive agent," or "active agent" as used interchangeably, means any organic or inorganic compound or substance having bioactivity and adapted or used for therapeutic purposes. Proteins, hormones, anti-cancer agents, small molecule chemical compounds and mimetics, oligonucleotides, DNA, RNA and gene therapies are included under the broader definition of "drug". As used herein, reference to a drug, as well as reference to other chemical compounds herein, is meant to include the compound in any of its pharmaceutically acceptable forms, including isomers such as diastereomers and enantiomers, salts, solvates, and polymorphs, particular crystalline forms, as well as racemic mixtures and pure isomers of the compounds described herein, where applicable.

A "water insoluble drug" or "poorly water soluble drug" is one having an aqueous solubility below 10 mg/mL.

The terms "effective amount" or "pharmaceutically effective amount" or "therapeutically effective amount" of a composition (or hydrogel or polymer), as provided herein, refer to a non-toxic but sufficient amount of the composition to provide the desired response, such as preventing, diminishing, or eliminating pain in a subject. The exact amount required will vary from subject to subject, depending on the species, age, and general condition of the subject, the severity of the condition being treated, the particular drug or drugs employed, specifics of the composition, mode of administration, and the like. An appropriate "effective" amount in any individual case may be determined by one of ordinary skill in the art using routine experimentation.

"Optional" or "optionally" means that the subsequently described circumstance may or may not occur, so that the description includes instances where the circumstance occurs and instances where it does not.

The term "substantially" in reference to a certain feature or entity means to a significant degree or nearly completely (i.e. to a degree of 85% or greater) in reference to the feature or entity.

The term "about", particularly in reference to a given quantity, is meant to encompass deviations of plus or minus five percent.

Additional definitions may also be found in the sections which follow.

Overview

The present application is based, at least in part, on the inventors' discovery of an in-situ gel forming composition.

The precursor compositions provided herein demonstrate rapid gelation, as well as beneficial adhesive properties, and good biocompatibility. By employing reactants having a particular degree of polymer modification, concentrations effective to favor both the formation of homogeneous solutions (i.e., dissolution) and rapid gelation, as well as particular pH conditions, the inventors have provided methods, liquid precursor gel-forming compositions, kits, and resulting hydrogels, among other things, having a number of beneficial features, to be described in greater detail below.

The hydrogels described herein are generally formed by reaction of hyaluronic acid having a particular degree of vinyl sulfone-modification with a thiol-functionalized polyethylene glycol. The resulting hydrogels are formed in-situ under mild conditions—without the need for initiators or accelerants or other deleterious additives. The features of the composition, related methods, uses, and kits, and the like will now be discussed in greater detail below.

Methods of Preparing Precursor Compositions Effective to Form In-Situ Gels Reactants/Components Vinyl-Sulfone Modified Hyaluronic Acid In preparing the instant in-situ forming gels, one of the reactants employed is hyaluronic acid modified by reaction with divinyl sulfone. See, e.g., FIG. 1, which provides a general reaction scheme for preparing vinyl-sulfone modified hyaluronic acid. Hyaluronic acid (HA) is a naturally occurring linear polysaccharide composed of alternating disaccharide units of N-acetyl-D-glucosamine and D-glucuronic acid joined by alternating β 1->3 glucuronidic and β 1->4 glucosaminidic bonds, so that the repeating unit is (1->4)-β-D-GlcA-(1->3)-β-D-GlcNAc. The hyaluronic acid for use in preparing one or more in-situ hydrogel forming compositions is derivatized with vinyl sulfone. See, for example, Examples 1, 2, and 3 which describe preparation of vinyl sulfone modified hyaluronic acid having varying levels of substitution, 11%, 14%, and 20%, respectively. In an exemplary derivatization reaction, the hyaluronic acid hydroxyl groups are transformed to (2-(vinylsulfonyl) ethoxy) groups by reaction with divinyl sulfone in the presence of base. The resulting activated hyaluronic acid is (2-(vinylsulfonyl)ethoxy)hyaluronic acid or HA-VS. For convenience, the material is typically referred to herein as vinyl-sulfone modified hyaluronic acid or simply "HA-VS". For preparing these rapid gelling compositions, the extent of vinyl sulfone substitution on the hyaluronic acid can range anywhere from 2% to 70%, although lower levels of polymer modification within this range are generally preferred. Exemplary vinyl-sulfone-modified hyaluronic acid will possess a vinyl-sulfone substitution level ranging from 7% to about 35%, or more preferably from 10% to 25%.

A 2% degree of modification or substitution means that an average of 2% of the hyaluronic acid disaccharide units contain a vinyl sulrone group Specifically, in a preferred embodiment, the hyaluronic acid possesses from about 10% to about 25% of its hydroxyl groups derivatized by an addition reaction with divinyl sulfone. The hyaluronic acid hydroxyl groups are transformed to (2-(vinylsulfonyl) ethoxy) groups. The resulting activated hyaluronic acid is referred to generally herein as (2-(vinylsulfonyl)ethoxy) hyaluronic acid or HA-VS. In particular, the hyaluronic acid may possess a degree of conversion of hydroxyl groups to (2-(vinylsulfonyl)ethoxy) groups within a range between any two of the foregoing percentages: e.g., from 10%-35%, for instance, from 11%-35%, or from 12-35%, and so forth. In particular, the hyaluronic acid may have a degree of vinyl sulfone substitution selected from the following percentages: 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, and 35%, along with ranges resulting from each and every combination of integers provided, e.g., from 10-15%, from 15-20%, from 20-25%, and so forth. In yet a more specific embodiment, the hyaluronic acid has a degree of conversion of hydroxyl groups to (2-(vinylsulfonyl)ethoxy) groups of about 10-25% per disaccharide repeat unit.

The degree of substitution/modification of hyaluronic acid can be determined by any of a number of suitable methods, e.g., NMR, UV, or IR analysis, or elemental analysis. A preferred method for calculating percent substitution of a polymer such as hyaluronic acid is NMR, e.g., proton NMR. See, e.g., Example 1 in which degree of hyaluronic acid modification was determined based upon the ratio of relative peak areas corresponding to the vinyl sulfone and the acetamide methyl group of the hyaluronic acid in the $^1$H NMR spectrum.

The vinyl-sulfone derivatized hyaluronic acid will typically possess an average molecular weight in the range of about 10,000 to about 2,000,000 daltons, Illustrative molecular weight ranges are from about 15,000 to 1,000,000 daltons, or from about 20,000 to 200,000 daltons. Additional suitable molecular weight ranges include from about 30,000 daltons to about 100,000 daltons, or from about 40,000 daltons to about 80,000 daltons. Molecular weights of hyaluronic acid are generally average molecular mass values, which can be determined, for example, by multi-angle laser light scattering exlusion chromatography (MALLS-SEC). Depending upon its source, hyaluronic acid may have a polydispersity ($M_w/M_n$) of up to around 3, or more preferably, up to around 2. Generally, the hyaluronic acid starting material will have a rather narrow molecular weight distribution, with values less than about 2.5, more preferably less than about 2. Exemplary polydispersities of hyaluronic acid range from about 1.02 to about 2.5, where the starting hyaluronic acid may possess a polydispersity of about 1.02, 1.05, 1.1, 1.2, 1.3, 1.3, 1.5, 1.6, 1.7, 1.8, 1.9, 2.0, 2.1, 2.2, 2.3, 2.4 or 2.5, or even greater.

Alternatively, a suitable hyaluronic acid starting material for derivatization may have an intrinsic viscosity, typically in centipoise, at a specific concentration in water, that corresponds to any one or more of the average molecular weight ranges provided above.

HA-VS having any combination of features described above (extent of modification, molecular weight, etc., is suitable for use in the compositions, kits, methods and uses provided herein.

Thiol-Functionalized Polyethylene Glycol (PEG)

Thiol-functionalized PEGs for use in forming the in-situ gel may be linear, branched (having two polymer arms), or multi-armed (e.g., having 3, 4, 5, 6, 7, 8 or more polymer arms extending from a central core). Illustrative core molecules for multi-armed PEGs include erythritol, pentaerythritol, trimethylolpropane, glycerol, glycerol dimer (3,3'-oxydipropane-1,2-diol), glycerol oligomers, sorbitol, hexaglycerol, and the like. Multi-arm PEG thiols such as the foregoing possess polyethylene glycol arms emanating from the central core molecule and possess two or more terminal thiol groups. Thiol functionalized PEGs can be prepared by derivatization of a commercially available PEG starting material or can be purchased directly from suppliers such as Pierce (Thermo Fischer Scientific), Laysan Bio, Inc. (Arab, Ala.), SunBio (PEG=SHOP, Korea), and the like.

A thiol-functionalized PEG comprises two or more thiol groups. Such thiol groups will react with a vinyl sulfone such as within a vinyl-sulfone derivatized hyaluronic acid. Illustrative thiol-functionalized PEGs include PEG-dithiol (HS-PEG-SH or HS—$CH_2CH_2$—$(OCH_2CH_2)_n$SH), 3-arm PEG-tri-thiol (glycerine core), 4-arm PEG-tetrathiol (pentaerythritol core), or 8-arm PEG-octa-thiol (hexaglycerine core). The foregoing multi-armed PEG reagents may also have fewer than all arms functionalized with thiol. Additional suitable thiol reagents having PEG as the central molecule are available from Laysan Bio (Arab, Ala.) and SunBio (PEG-SHOP, Korea), as well as aromatic dithiols such as those available from NanoScience. Preferred PEG-thiols will possess a number of thiol groups selected from 2, 3, 4, 5, 6, 7, and 8. Also suitable are polyethylene glycol molecules having from 2-8 pendant thiol groups substituted on the linear polyethylene glycol chain.

The molecular weight of the PEG thiol is typically less than that of the vinyl-sulfone modified hyaluronic acid. Generally, the molecular weight of the PEG thiol ranges from about 200 to about 20,000 daltons. Additional exemplary molecular weight ranges for the PEG thiol crosslinker are from about 1,000 to about 10,000 daltons (e.g., having a molecular weight of about 1 kD, 2 kD, 3 kD, 4 kD, 5 kD, 6 kD, 7 kD, 8 kD, 9 kD, or 10 kD, where kD equals kilodalton) or even from about 1,000 to 5,000 daltons. Thus, PEG thiols having a molecular weight falling within a range between any of the foregoing molecular weights are suitable for use in forming the present hydrogels. For example, the PEG thiol may have a molecular weight between about 500 to 10,000 daltons, or between about 1000 and 10,000 daltons, or between about 2,000 and 9,000 daltons, or between about 3,000 and 8,0000 daltons, and so forth. Exemplary molecular weights for a crosslinker such as PEG dithiol, or any of the other suitable crosslinkers described above, include about 3350, 3400, and 5000 daltons, among others.

PEG thiols having any combination of features such as described above (architecture, e.g., linear or branched, number of thiol groups, molecular weight, etc., are suitable for use in the compositions, kits, methods, and uses provided herein.

Bioactive Agents

The hydrogels, hydrogel precursors, and related compositions and/or kits provided herein may optionally comprise a bioactive agent. Bioactive agents include small molecules, proteins, antibodies, cells, growth factors, etc., such as those described below.

Bioactive agents that may be included in the kits, compositions, and combinations provided herein include antimicrobials, antibiotics, analgesics, antibiotics, antiproliferative/antimitotic agents including natural products such as vinca alkaloids (e.g. vinblastine, vincristine, and vinorelbine), paclitaxel, epidipodophyllotoxins (e.g. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase); antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine [cladribine]); platinum coordination complexes (cisplatin, carboplatin), procarbazine, hydroxyurea, mitotane, aminoglutethimide; hormones (e.g. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (such as brefeldin A); anti-inflammatory agents such as adrenocortical steroids (hydrocortisone, hydrocortisone acetate, cortisone acetate, tixocortol pivalate, prednisolone, methylprednisolone, prednisone, triamcinolone acetonide (or any other pharmaceutically acceptable salts of triamcinolone), triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, and fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate. Beclomethasone dipropionate monohydrate, flunisolide, fluticasone propionate, mometasone furoate monohydrate, triamcinolone acetonide, fluticasone, furoate, non-steroidal agents (salicylic acid derivatives e.g. aspirin); para-aminophenol derivatives, i.e. acetominophen; indole and indene acetic acids (indomethacin, sulindac, and etodolac), heteroaryl acetic acids (tolmetin, diclofenac, and ketorolac), arylpropionic acids (ibuprofen and derivatives), anthranilic acids (mefenamic acid and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive (cyclosporine, tacrolimus (FK-506), sirolimus (rapamycin), azathioprine, mycophenolate mofetil); mitogenic or morphogenic growth factor proteins, peptides or mimetics; vascular endothelial growth factor (VEGF), fibroblast growth factor (FGF), transforming growth factor-β (TGF-β) superfamily members including TGF-β's and bone morphogenic proteins (BMP's) such as BMP-2, 3, 4, 5, 6, 7, 8; insulin and insulin-like growth factors (IGF's), hepatocyte growth factor (HGF), epidermal growth factors (EGF's), Hedgehog proteins (SHH and IHH), activins, inhibins, demineralized bone (DBM) and platelet-derived growth factors (PDGF's), hematopoietic growth factors (G-CSF, CSF-1, GM-CSF, erythropoietin, cytokines and lymphokines including the interleukin family (IL-1 to 34)), interferons, nerve growth factors (NGF's), neutralizing, antagonist or agonist antibodies, growth factor receptor agonists or antagonists, nitric oxide donors; anti-sense oligonucleotides, transcription factors, signaling cascade mediators, and combinations thereof.

Antibiotics include antibiotics of the lincomycin family (referring to a class of antibiotic agents originally recovered from *streptomyces lincolnensis*); antibiotics of the tetracycline family (referring to a class of antibiotic agents originally recovered from *streptomyces aureofaciens*); sulfur-based antibiotics such as the sulfonamides; and so forth. Exemplary antibiotics of the lincomycin family include lincomycin itself (6,8-dideoxy-6-[[(1-methyl-4-propyl-2-pyrrolidinyl)-carbonyl]amino]1-thio-L-threo-D-galacto-octopyranoside), clindamycin, the 7-deoxy, 7-chloro derivative of lincomycin (e.g., 7-chloro-6,7,8-trideoxy-6-[[(1-methyl-4-propyl-2-pyrrolidinyl) carbonyl]amino]-1-thio-L-threo-D-galacto-octopyranoside), and pharmacologically acceptable salts and esters thereof. Exemplary antibiotics of the tetracycline family include tetracycline itself 4-(dimethylamino)-1,4,4α,5,5α,6,11,12α-octahydro-3,6,12,12α-pentahydroxy-6-methyl-1,11-dioxo-2-naphthacenecarboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium. Antimicrobials and/or antibiotics further include compounds such as erythromycin, bacitracin, neomycin, penicillin, polymyxin B, tetracyclines, viomycin, chloromycetin and streptomycins, cefazolin, ampicillin, azactam, tobramycin, clindamycin and gentamycin.

Analgesics include compounds such as lidocaine, benzocaine, and marcaine.

A hydrogel as provided herein may also include living cells. Exemplary living cells include stem cells, parenchimal stem cells, blood-derived cells, and bone marrow cells.

Additional bioactive agents include but are not limited to those which inhibit one or a combination of processes including but not limited to cell division, cell secretion, cell migration, cell adhesion, cytokine, chemokine (or other inflammatory activator) production and/or release, angiogenesis, and/or free radical formation and/or release, and/or coagulation cascade. In particular, the compositions provided herein may provide involves pharmacological alteration of cellular and/or non-cellular processes involved in the development and/or maintenance of surgical adhesions. Additionally, the instant compositions may provide pharmacological alteration of cellular and/or non-cellular processes involved in the development and/or maintenance of restenosis. Thus, additional bioactive agents include but are not limited to those which inhibit one or a combination of processes including but not limited to cell division, cell secretion, cell migration, cell adhesion, cytokine, chemokine (or other inflammatory activator) production and/or release, angiogenesis, and/or free radical formation and/or release. Additionally, bioactive agents for use herein may inhibit or affect other processes involved in the scarring process. The compositions provided herein may also be effective to produce pharmacological alteration of cellular and/or non-cellular processes which increase the development of fibrosis. Thus, bioactive agents further include but are not limited to those which increase one or a combination of processes including but not limited to cell division, cell secretion, cell migration, cell adhesion, cytokine, chemokine (or other inflammatory activator) production and/or release, angiogenesis, and/or free radical formation and/or release. Additional bioactive agents may increase or affect other processes involved in the scarring process such that the compositions provided herein may be hemostatic agents and/or adhesion prevention agents, such that the addition of a drug can effect an increase or decrease in fibrosis, and/or result in tissue augmentation and/or increase or reduction in surgical adhesions depending on the drug mechanism. For example, a drug which decreases fibrosis will be expected to reduce surgical adhesions. Furthermore, the drug-loaded formulation may increase the sealant and/or hemostatic properties of the formulation, especially when the agent acts to increase fibrosis. Additionally, the compositions provided herein may provide pharmacological alteration of cellular and/or non-cellular processes involved in the development and/or maintenance of surgical adhesions or restenosis or in more general terms inhibit one or more processes involved in fibrosis. Thus, additional pharmacological agents include but are not limited to those which inhibit one or a combination of processes such as cell division, cell secretion, cell migration, cell adhesion, extracellular matrix production, cytokine (e.g., TNF alpha, IL-1, IL-6), or other inflammatory activator, e.g., chemokines (e.g., MCP-1 or IL-8)) production and/or release, angiogenesis, and/or free radical formation and/or release. Suitable fibrosis-, adhesion- or stenosis-inhibiting agents are disclosed in detail in, for example, WO2004/060346, WO 2005/051452, WO 2006/13547, and WO 2007/089878, and are also readily determined based upon the in vitro and in vivo (animal) models such as those provided in, e.g., WO2004/060346. The foregoing references are included herein by reference in their entireties with respect to active agents described therein.

Within other embodiments, the active agent may be a fibrosing agent, fibrosis-inducing agent and/or adhesion-inducing agent, representative examples of which may be found, without limitation, in International Publication Nos. WO 2005/046746, WO 2005/046747, and WO 2006/124021, the entire disclosures of which are included herein by reference with respect to such compounds.

Additional drugs suitable for use include those set forth in detail in, e.g., WO2004/060346. For instance, exemplary compositions may comprising any one or more of the following: a cell cycle inhibitor; paclitaxel; doxorubicin; mitoxantrone; podophyllotoxin (e.g., etoposide); an immunomodulatory agent, everolimus; tacrolimus; biolimus; a heat shock protein 90 antagonist; geldanamycin; a HMG CoA Reductase inhibitor; simvastatin; an IMPDH Inhibitor; mycophenolic acid; 1-alpha-25 dihydroxy vitamin D3; an antimycotic agent such as sulconizole; a P38 MAP kinase inhibitor such as SB220025; component of the extracellular matrix such fibronectin; collagen; fibrin; fibrinogen; polylysine; chitosan; N-carboxybutylchitosan; a RGD protein; an inflammatory cytokine selected from the group consisting of TGFb, PDGF, VEGF, bFGF, TNFa, NGF, GM-CSF, IGF-a, IL-1, IL-8, IL-6, and growth hormone; a connective tissue growth factor (CTGF); a bone morphogenic protein (BMP) selected from BMP-2, BMP-3, BMP-4, BMP-5, BMP-6, or BMP-7; bleomycin; an analogue or derivative of bleomycin; a proliferative agent that stimulates cellular proliferation; dexamethasone and analogues and derivatives thereof; 17-.beta.-estradiol and analogues and derivatives thereof; estradiol and analogues and derivatives thereof; diethylstibesterol and analogues and derivatives thereof; cyclosporine A and analogues and derivatives thereof; all-trans retinoic acid (ATRA) and analogues and derivatives thereof. Additional bioactive agents that may be employed in the present disclosure are set forth in WO 2005/046746, WO 2005/046747, WO 2006/124021, WO2004/060346, WO 2005/051452, WO 2006/13547, and WO 2007/089878, which are incorporated herein by reference in their entireties with respect to bioactive agents described therein.

In particular, the drug may be one or more hemostatic proteins, including without limitation, thrombin, fibrin, fibrinogen, blood factors, coagulation factors (e.g., Factors VIII and XIII).

In one preferred embodiment, the hydrogel precursor composition comprises a corticosteroid. Examples of suitable corticosteroids include hydrocortisone, hydrocortisone acetate, cortisone acetate, tixocortol pivalate, prednisolone, methylprednisolone, prednisone, triamcinolone, triamcinolone salts such as triamcinolone acetonide, triamcinolone benetonide, triamcinolone furetonide, triamcinolone hexacetonide, triamcinolone diacetate, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, beclomethasone dipropionate monohydrate, flunisolide, fluticasone propionate, mometasone furoate monohydrate, and fluticasone furoate.

One preferred compound for use in a hydrogel formulation as provided herein is triamcinolone (11β,16α)-9-fluoro-11,16,17,21-tetrahydroxypregna-1,4-diene-3,20-dione), or a pharmaceutically acceptable salt, ester, or solvate thereof. The structure of triamcinolone acetonide is shown below.

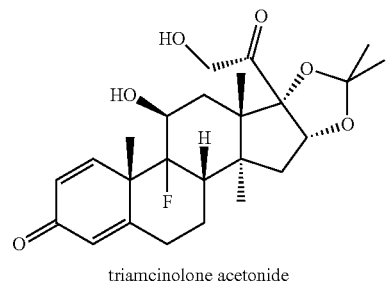

triamcinolone acetonide

The bioactive agent will typically be admixed, suspended in, or entrapped within an in-situ hydrogel-forming composition as provided herein. Alternatively, the bioactive agent may be in the form of a polymer conjugate, or, may be covalently attached, in a releasable fashion, to a component used to prepare the hydrogel, e.g., the modified hyaluronic acid or thiol-functionalized PEG.

Method of Preparing In-Situ Hydrogels

The rapid gelling compositions provided herein are typically formed by reacting the vinyl-sulfone modified hyaluronic acid and PEG thiol under conditions effective to form a rapidly-forming gel. Generally, the relative amounts of reagents and reactive groups, along with reaction conditions, are adjusted to provide optimal reaction. The hydrogel precursor solution is prepared under mild and controlled conditions, without the need for external energy sources. See, e.g., Examples 1-21. One or more of the components of the kit and/or liquid composition are preferably in sterile form. In a preferred embodiment, the HA-VS is sterile. In yet a further preferred embodiment, the thiol-functionalized polyethylene glycol and buffer are also sterile.

Method 1

The precursor compositions are generally prepared as follows, although it will be appreciated that the methods described may be suitably modified by one skilled in the art to arrive at the compositions, kits, materials, and hydrogels provided herein, based upon the instant disclosure. In the first exemplary method, vinyl-sulfone modified hyaluronic acid as described above is generally dissolved in an aqueous medium such as water, saline, or the like. That is to say, any HA-VS having the features described herein may be used. For instance, an exemplary vinyl-sulfone modified hyaluronic acid possesses 11% vinyl sulfone substitution and possesses a molecular weight of 100 kilodaltons. The aqueous medium will generally have a pH ranging from about 5-7, and may, in certain instances, be slightly acidic. Ideally, the vinyl-sulfone modified hyaluronic acid is provided as a highly concentrated solution to the extent possible based upon its aqueous solubility, to enable rapid gelation. Typically, the HA-VS is provided as a solution at a concentration of about 10-300 mg/mL. Additional exemplary ranges of suitable concentrations include the following: from about 15-250 mg/mL, or even more preferably from about 20-200 mg/mL. For example, the HA-VS may possess a concentration selected from: 10 mg/mL, 15 mg/mL, 20 mg/mL, 25 mg/mL, 30 mg/mL, 50 mg/mL, 75 mg/mL, 100 mg/mL, 125 mg/mL, 150 mg/mL, 175 mg/mL, 200 mg/mL, 225 mg/mL, 250 mg/mL, or 300 mg/mL. Additionally, the HA-VS may possess a concentration falling within a range derived from a combination of any two of the foregoing concentrations, e.g., between 15 mg/mL and 125 mg/mL, or between 20 mg/mL and 150 mg/mL, and so forth. A high concentration is advantageous with respect to rapid gel formation of the resulting precursor composition upon mixing.

Once dissolved, the resulting aqueous solution of vinyl sulfone-modified hyaluronic acid is then typically sterilized. Sterilization for any of the sterilization steps described herein may be carried out by, for example, heat treatment, high-pressure vapor sterilization (e.g. autoclave sterilization), ethylene oxide gas (EOG) sterilization, supercritical carbon dioxide sterilization, radiation sterilization or sterile filtration. Radiation sources includes $\alpha$-rays, $\beta$-rays, $\gamma$-rays, neutron beams, electron beams, and X-rays. In certain embodiments, $\gamma$-ray sterilization or electron beam sterilization is employed, in particular for solids. In one preferred approach for sterilizing the HA-VS solution, sterilization is by autoclaving. Although reference may be made to any one or more components of the kit or compositions provided herein in sterile form, it is to be understood that such components may or may not be sterile.

The thiol-functionalized PEG is then added to the sterile vinyl-sulfone functionalized hyaluronic acid solution, preferably as a sterile powder. Generally, the amount of thiol-functionalized PEG relative to the vinyl sulfone functionalized hyaluronic acid is in range from about 1:1 (w/w) to about 2:1 (w/w). The components are mixed until the PEG thiol is dissolved. Although the thiol-functionalized PEG may be added as an aqueous solution, it is preferably added as a solid due to its high solubility in aqueous media, since addition in solid form prevents further dilution of the reaction mixture, which can slow gelation times.

The resulting thiol-functionalized PEG-vinyl sulfone-hyaluronic acid solution is then mixed with buffer to form a rapid-gelling precursor composition. The buffer is generally at a pH from about 7-12. Preferably, the buffer is at a pH of from about 7.5 to 11, or even more preferably from about 8.0 to 10.5. Illustrative pHs of the buffer solution include 7, 7.5, 8, 8.5, 9, 9.5, 10, 10.5, 11, 11.5, and 12, or any other pH within the foregoing range. Suitable buffers include basic buffers such as sodium phosphate, sodium carbonate, imidizole, Tris, HEPES, boric acid, MOPS, and the like. A preferred buffer is sodium phosphate. The buffer solution will generally have a strength in a range of from about 30 to 1000 millimolar (mM). Preferably, the buffer strength is from about 35 to 800 mM, or even more preferably from about 40-600 mM. Example 4 demonstrates the effect of buffer (e.g., pH and concentration) upon gelation. As can be seen, solutions were prepared which underwent gelation within less than 2 minutes from mixing (times ranged from instantaneous to 1 minute 40 seconds).

The concentration of the PEG-thiol reactant in the resulting in-situ hydrogel forming precursor composition will typically be in a range from about 10 to 600 mg/mL. Exemplary concentrations are from about 15-500 mg/mL or more preferably from about 20 to 400 mg/mL.

The resulting precursor solution generally forms a gel within from seconds (e.g., 5 seconds) to about 1 hour of mixing. Preferably, the solution will form a gel within about 15 minutes (i.e., anywhere from about 5 seconds to 15 minutes after mixing, or within 30 seconds to 15 minutes after mixing), or even more preferably, within about 10 minutes, or even more preferably, within about 5 minutes, or even more preferably, within about 3 minutes of mixing.

Rapid-gelling compositions were prepared using both linear PEG-dithiol and 4-arm PEG tetrathiol as described in Example 7. Each of the compositions tested gelled within a minute of mixing while burst pressures (indicating gel strength) varied from about 0.450 to 0.685 PSI.

Method 2

In a slightly modified approach to method 1, a small amount of soluble PEG-thiol is added to the vinyl-sulfone modified hyaluronic acid solution to lessen the time required for dissolution. The soluble PEG-thiol that is added is preferably sterile.

As described for method 1 above, vinyl-sulfone modified hyaluronic acid is generally dissolved in an aqueous medium such as water, saline, or the like. The aqueous medium will generally have a pH ranging from about 5-7, and may, in certain instances, be slightly acidic. Ideally, the vinyl-sulfone modified hyaluronic acid is provided as a highly concentrated solution to the extent possible based upon its aqueous solubility, to enable rapid gelation. Typically, the HA-VS is provided as a solution at a concentration of about 10-300 mg/mL. Additional exemplary ranges of suitable concentrations include the following: from about 15-250 mg/mL, or even more preferably from about 20-200 mg/mL. A high concentration is advantageous with respect to rapid gel formation of the resulting precursor composition upon mixing.

A small portion of the thiol-functionalized PEG, e.g., from about 0.1 wt % to about 4 wt % (wt/wt thiol-functionalized PEG to HA-VS) is then added to the vinyl-sulfone functionalized hyaluronic acid solution, preferably as a powder. Additional exemplary amounts of thiol-functionalized PEG that may be added include from about 0.1 wt % to about 3.5 wt %, or from about 0.1 to 2.5% (wt/wt thiol-functionalized PEG to HA-VS). The components are mixed until they are dissolved.

The resulting solution containing vinyl sulfone functionalized hyaluronic acid and a portion of the total amount of thiol-functionalized PEG to be added is then typically sterilized as described above. In a preferred approach, the solution is autoclaved.

To the resulting, typically sterilized solution, is then added the remaining amount if thiol-functionalized PEG, again preferably as a sterile powder. The components are mixed until the PEG thiol is dissolved. As in method 1, although the thiol-functionalized PEG may be added as an aqueous solution, it is preferably added as a solid due to its high solubility in aqueous media, since addition in solid form prevents further dilution of the reaction mixture, which can slow gelation times.

The resulting thiol-functionalized PEG-vinyl sulfone-hyaluronic acid solution is then mixed with buffer as described above under method 1 to form a rapid-gelling precursor composition.

In both methods, generally, the concentrations of both the vinyl sulfone functionalized hyaluronic acid and the thiol-functionalized PEG in the final liquid rapid-gelling precursor solution, after additional of buffer, range from about 2% to about 8% weight/volume. Exemplary concentrations of each reactant then can be selected from about 2%, 3%, 4%, 5%, 6%, 7% and 8% weight/volume, including all ranges there-between. In a preferred embodiment, the concentration of both the vinyl sulfone functionalized hyaluronic acid and the thiol-functionalized PEG in the final liquid rapid-gelling precursor solution, after addition of buffer, ranges from about 2% to about 6% weight/volume.

In one or more particular embodiments, the rapid-gelling precursor composition contains an active agent as described above. Preferred classes of bioactive agents include steroids, growth factors, anti-proliferative agents, and antibiotics. One particularly advantageous class of active agent for incorporation into the instant compositions are corticosteroids. Illustrative corticosteroids include but are not limited to the following: triamcinolone, triamcinolone salts such as triamcinolone acetonide, triamcinolone hexacetonide, triamcinolone benetonide, triamcinolone furetonide, and triamcinolone diacetate and the like, and methylprednisolone. Generally, the rapid gelling precursor composition contains from about 0.01% by weight to about 20% by weight bioactive agent, depending on its potency, based upon the overall composition. Illustrative amounts of bioactive agent contained in the in-situ forming hydrogel are from about 10% to about 20% by weight, e.g., for a less potent bioactive agent, and from about 0.01% to about 10% by weight, or from about 0.01% to about 5%, or from about 0.01% to about 3%, or from about 0.1 to about 2% bioactive agent, or even from about 0.1 to about 1% bioactive agent, e.g., for a more potent bioactive agent such as triamcinolone acetonide.

The bioactive agent can be mixed with one of the reactants (assuming no stability or reactivity issues) or the buffer component, or alternatively, added at the time of mixing. That is to say, a bioactive agent can be incorporated at any stage during the preparation of the precursor in-situ gel-forming composition.

The precursor gel-forming composition may additionally contain one or more additives such as preservatives, defoamers, pore forming agents, plasticizers, penetration enhancers, colorants, wettings agents, leveling agents, hydrating agents, thickeners, fillers, opacifying agents, and absorbents, although any such additive should be biocompatible and when included in the precursor composition, be deliverable by any of the means described herein.

Kits

The above components may be supplied in the form of a kit, e.g., for use in a clinical setting. For example, such a kit may contain, in a first container, a sterile or non-sterile aqueous solution of vinyl-sulfone derivatized hyaluronic acid as described above. Alternatively, the vinyl-sulfone derivatized hyaluronic acid may be supplied as a solid (e.g., as a powder), which is then dissolved in an aqueous medium as described above prior to mixing with the thiol-functionalized PEG. In the latter embodiment, a suitable volume of the aqueous medium to provide a HA-VS solution within the concentration ranges set forth above would generally also be provided with the kit. Also comprised within the kit in a second container is the thiol-functionalized PEG, preferably provided as a solid in sterile form. The thiol-functionalized PEG may also be provided in the second container as an aqueous solution, although as described above, solid form is preferable so as not to further dilute the reactants upon mixing. Additionally provided, in a third container, is a sterile or non-sterile buffer solution, e.g., containing a buffer as previously described, e.g., a 30-1000 mM buffer solution in a pH range from about 7-12.

In accordance with the methods previously described, in an alternative embodiment, the first container may contain a sterile or non-sterile aqueous solution of vinyl-sulfone derivatized hyaluronic combined with a small amount of thiol-functionalized PEG, e.g., from about 0.1 wt % to about 4 wt % (wt/wt thiol-functionalized PEG to HA-VS), or from about 0.1 wt % to about 3.5 wt %, or from about 0.1 to 2.5% (wt/wt thiol-functionalized PEG to HA-VS).

The kit may further comprise a bioactive agent which generally will typically be packaged separately and admixed with the other kit components immediately prior to use. Such bioactive agent is preferably although not necessarily provided as a solid.

Also included in the kit are instructions for mixing and subsequent use.

The containers as described above include any suitable, pharmaceutically acceptable packaging container for housing the above components. For example, suitable containers include glass, plastic, foil and film-formed containers such as blister packs, bottles, pouches, ampules, vials, syringes (single, dual or multiplets), pipettes, applicators, tubes and the like.

The foregoing components, for example, may each be packaged in a syringe, which is generally sealed, e.g., with a vented cap. The syringe can be made from plastic (e.g. polypropylene, polycarbonate, polystyrene) or glass or any other pharmaceutically acceptable material. The volume of the syringe may range from 0.5 mL to 20 mL, with preferable volumes being 1 mL, 2 mL, 3 mL, 4 mL, 5 mL, 6 mL and 7 mL.

The syringe may then be placed in a container, such as a foil pouch which is then sealed. The pouch may be vacuum sealed, sealed under an inert gas such as nitrogen or argon, or sealed following one or more vacuum/back fill cycles where the back fill gas is an inert gas such as nitrogen or argon. For the pouch sealed under one or more vacuum/back fill cycles, the cycle can be adjusted such that the pouch is finally sealed under either vacuum or an inert gas. The pouch may optionally contain a dessicant and/or an oxygen scavenger.

Method of Application

The components described herein may be applied to any of a number of body sites. Exemplary sites include skin, mucous membranes, body cavities, internal surfaces of bones, tissue sites, voids, artery, vein, ducts, and the like.

The rapid-gelling composition provided herein, or alternatively, its components, may be applied to a treatment site using, for example, a syringe (with or without a needle), a catheter, a trocar, a gas-assisted spray device, a manual spray applicator, an endoscopic gas assisted applicator, or the like. Illustrative spray devices include EASY SPRAY Spray Set (Baxter AG, USA), FibriJet (Micromedics Inc. USA) and so on. The FibriJet series includes both a standard atomization applicator kit (FibriJet® Manual Spray Applicator) as well as a gas assisted atomization applicator kit (FibriJet® Gas Assisted Spray Applicator), both suitable for applying the subject rapid-gelling compositions.

Uses

The rapid gelling compositions described herein may be used in a number of applications, e.g., for embryonic development, tissue organization, wound healing, angiogenesis and tumorigenesis. See D. D. Allison and K. J. Grande-Allen, *Tissue Engineering*, Vol. 12, Number 8, 2131-2140 (2006); G. D. Prestwich et al, *Tissue Engineering*, Vol. 12, Number 8, 2171-2180 (2006); G. D. Prestwich et al, *Tissue Engineering*, Vol. 12, Number 12, 3405-3416 (2006).

For example, the rapid gelling, sprayable compositions provided herein, optionally containing one or more bioactive agents, may be used as adhesive compositions, e.g., as tissue adhesives and sealants that may be used for various applications, including preventing bleeding, covering open wounds, and other biomedical applications. For instance, the subject compositions may be used in preventing surgical adhesions in the lumbar, dural, nasal, sinus, abdominal, tendon, and joint regions of the body. These compositions may be used in, for example, apposing surgically incised or traumatically lacerated tissues, retarding blood flow such as those from wounds, preventing restenosis or blood clotting, drug delivery; dressing burns, to effect hemostasis, and aiding repair and regrowth of living tissue. The compositions may be used for supplementing or inducing and regenerating damaged organs or tissues in a mammalian subject, such as a human. The composition is decomposed or absorbed, or alternatively, remains in the subject (e.g., mammalian subject) without having adverse influences on subject when embedded or contained therein. When employed as a sealant, the rapid-gelling composition is useful in the following regions of the body: vascular, dural, lung, bowel, bladder, intestine, ocular, and topical. For example, when employed as a vascular sealant, the subject composition may be used as a vein to vein sealant, an artery to vein sealant, a vein to artery sealant, a vein to synthetic polymer sealant, an artery to synthetic polymer sealant, a synthetic polymer to artery sealant, and a synthetic polymer to vein sealant. The compositions may also be used for arthroscopic or open joint surgery, e.g., to repair tissue of the joint (i.e., cartilage).

When the goal is to have the composition adhere to a tissue surface, the composition must have sufficient adhesive strength and sufficient cohesive strength such that adhesion to the tissue can occur without the composition either breaking or tearing and falling off the tissue to which it was applied. The adhesive strength of the composition refers to the ability of the composition to remain attached to the surface upon which it was applied, while the cohesive strength of the composition refers to the ability of the composition to remain as a single entity when external forces are applied to the composition. To measure the combination of adhesive and cohesive strength, a burst test may be carried out (see, e.g., Example 5). If a composition possesses a burst pressure of less than 0.2 PSI, then the composition is characterized as possessing a relatively weak cohesive/adhesive strength. The greater the burst strength exhibited by the composition, the greater the adhesive/cohesive strength of the composition. The hydrogel compositions provided herein possess good adhesive and adhesive strength.

The subject rapid-gelling compositions may also be used as tissue fillers, dermal fillers, bulking agents, e.g., as a urethral or a esophageal bulking agent, and embolic agents as well as agents to repair cartilage defects/injuries and agents to enhance bone repair and/or growth.

The subject rapid-gelling compositions may also be used as drug delivery vehicles, for example, to locally delivery a bioactive agent topically, intramuscularly, intra-articularly, subcutaneously, to the ocular region, intradermally, to treat in-bone defects, in cartilage defects, in tissue voids, and to in-body lumens.

The subject compositions may also be used in the treatment of osteoarthritis or rheumatoid arthritis, or for other inflammatory arthritides such as gout or calcium pyrophosphate deposition disease (e.g., by injection into the intra-articular space of a joint), or in the reduction or prevention of adhesions that can form following a surgical procedure.

The present application will now be described in connection with certain embodiments, which are not intended to limit the scope of the invention. On the contrary, the present application covers all alternatives, modifications, and equivalents as included within the scope of the claims. Thus, the following will illustrate the practice of the present application, for the purposes of illustration of certain embodiments and is presented to provide what is believed to be a useful and readily understood description of its procedures and conceptual aspects.

Exemplary Aspects and Embodiments

The following are illustrative aspects and embodiments in accordance with the teachings provided herein.

Aspect 1

In a first aspect, the present disclosure provides a kit comprising:

(i) a first container comprising an aqueous solution of vinyl sulfone-derivatized hyaluronic acid ("HA-VS") at a concentration of from about 10-300 mg/mL, where the HA-VS has from about 2%-70% of its hydroxyl groups substituted with vinyl sulfone, (ii) a second container comprising a thiol-functionalized polyethylene glycol having from 2 to 8 thiol groups, and (iii) a third container comprising a 30-1000 mM buffer solution at a pH ranging from about 7-12, in an amount effective, when mixed with the contents of the first and second containers, to provide a solution having a HA-VS concentration of 2-8% (w/v) and a thiol-functionalized polyethylene glycol concentration of 2-8% (w/v), wherein the components of the first, second and third containers, when combined, are effective to form a gel within from about 5 seconds to 1 hour of mixing. (Any one or more of the HA-VS, the thiol-functionalized polyethylene glycol, and the buffer solution may be in sterile form).

Aspect 2

In a second aspect, the present disclosure provides a liquid composition capable of forming a hydrogel upon mixing of its components. The liquid formulation is formed from the combination of (i) an aqueous solution of vinyl sulfone-derivatized hyaluronic acid ("HA-VS") at a concentration of from about 10-300 mg/mL, where the HA-VS has from about 2%-70% of its hydroxyl groups substituted with vinyl sulfone, (ii) a thiol-functionalized polyethylene glycol having from 2 to 8 thiol groups, and (iii) a 30-1000 mM buffer solution at a pH ranging from about 7-12, where the concentration of the thiol-functionalized polyethylene glycol in the liquid composition ranges from about 4-300 mg/mL, and the sprayable liquid composition is effective to form a gel within from about 5 seconds to about 1 hour of mixing components (i), (ii) and (iii). (Any one or more of the HA-VS, the thiol-functionalized polyethylene glycol, and the buffer solution may be in sterile form).

Aspect 3

In a third aspect, provided is a method of forming a sprayable liquid composition capable of in-situ gel formation. The method comprises the steps of:

(i) adding a thiol-functionalized polyethylene glycol having from 2 to 8 thiol groups to an aqueous solution of vinyl sulfone-derivatized hyaluronic acid ("HA-VS") having a concentration of from about 4-300 mg/mL, where the HA-VS has from about 2% to 70% of its hydroxyl groups substituted with vinyl sulfone, to thereby dissolve the thiol-functionalized polyethylene glycol to form a vinyl sulfone-derivatized hyaluronic acid-thiol-functionalized polyethylene glycol-containing solution, and (ii) combining the solution from step (i) with a 30-1000 mM buffer solution at a pH ranging from about 7-12, to thereby form a liquid composition having a HA-VS concentration of 2-8% (w/v) and a thiol-functionalized polyethylene glycol concentration of 2-8% (w/v), wherein the liquid composition is effective to form a gel within from about 5 seconds to about 1 hour of mixing.

Aspect 4

In a fourth aspect, provided is a method of forming a liquid composition capable of in-situ gel formation, where the method comprises the steps of:

(i) adding a portion of an overall amount of thiol-functionalized polyethylene glycol, preferably in sterile form, to an aqueous solution of vinyl sulfone-derivatized hyaluronic acid ("HA-VS") having a concentration of from about 10-300 mg/mL, where the HA-VS has from about 2%-70% of its hydroxyl groups substituted with vinyl sulfone, to thereby form a solution, (ii) preferably sterilizing the solution from step (i), (iii) adding to the solution from step (i) or step (ii) if conducted, the remaining amount of thiol-functionalized polyethylene glycol, where the thiol-functionalized polyethylene glycol has from 2 to 8 thiol groups, to thereby dissolve the remaining amount of thiol-functionalized polyethylene glycol to form a vinyl sulfone-derivatized hyaluronic acid-thiol-functionalized polyethylene glycol-containing solution, and (iv) mixing the vinyl sulfone-derivatized hyaluronic acid-thiol-functionalized polyethylene glycol-containing solution with a preferably sterile 30-1000 mM buffer solution at a pH ranging from about 7-12, to thereby form a liquid composition having a HA-VS concentration of 2-8% (w/v) and a thiol-functionalized polyethylene glycol concentration of 2-8% (w/v), where the liquid composition is effective to form a gel within from about 5 seconds to about 1 hour of mixing.

Embodiment 1

In an embodiment directed to any one or more of Aspects 1-4, the vinyl sulfone-derivatized hyaluronic acid possesses from about 7%-35%, or from 10% to 25%, of its hydroxyl groups substituted with vinyl sulfone.

Embodiment 2

In a second embodiment directed to any one or more of Aspects 1-4, and also combinable with Embodiment 1, the thiol-functionalized polyethylene glycol possesses a number of thiol groups selected from 2, 3, 4, 5, 6, 7, and 8.

Embodiment 3

In a third embodiment directed to any one or more of Aspects 1-4, and also combinable with Embodiment and/or Embodiment 2, the thiol-functionalized polyethylene glycol possesses a number of thiol groups selected from 2, 3, and 4.

Embodiment 4

In a fourth embodiment directed to any one or more of Aspects 1-4, and also combinable with any one or more of Embodiments 1-3, the vinyl sulfone-derivatized hyaluronic acid has an average molecular weight ranging from about 10,000 to about 2,000,000 daltons, or from about 15,000 to about 1,000,000 daltons, or from about 20,000 to about 200,000 daltons.

Embodiment 5

In a fifth embodiment directed to any one or more of Aspects 1-4, and also combinable with any one or more of Embodiments 1-3, the vinyl sulfone-derivatized hyaluronic acid has an average molecular weight of about 100,000 daltons.

Embodiment 6

In a sixth embodiment directed to any one or more of Aspects 1-4, and also combinable with any one or more of Embodiments 1-5, the thiol-functionalized polyethylene glycol is linear.

Embodiment 7

In a seventh embodiment directed to any one or more of Aspects 1-4, and also combinable with any one or more of Embodiments 1-6, the thiol-functionalized polyethylene glycol is branched.

Embodiment 8

In an eighth embodiment directed to any one or more of Aspects 1-4, and also combinable with any one or more of Embodiments 1-7, the thiol-functionalized polyethylene glycol has an average molecular weight of from about 1,000 to about 10,000 daltons.

Embodiment 9

In a ninth embodiment directed to any one or more of Aspects 1-4, and also combinable with any one or more of Embodiments 1-8, the molecular weight of the thiol-functionalized polyethylene glycol is less than the molecular weight of the vinyl sulfone-derivatized hyaluronic acid.

Embodiment 10

In a tenth embodiment directed to any one or more of Aspects 1-4, and also combinable with any one or more of Embodiments 1-9, the aqueous solution of vinyl sulfone-derivatized hyaluronic acid ("HA-VS") has a concentration ranging from about 20-200 mg/mL.

Embodiment 11

In an eleventh embodiment directed to any one or more of Aspects 1-4, and also combinable with any one or more of Embodiments 1-10, the thiol-functionalized polyethylene glycol is in the form of a powder.

Embodiment 12

In an twelfth embodiment directed to any one or more of Aspects 1-4, and also combinable with any one or more of Embodiments 1-11, the amount of thiol-functionalized polyethylene glycol relative to vinyl sulfone-derivatized hyaluronic acid ranges from about 1:1 (w/w) to about 0.4:1 (w/w).

Embodiment 13

In an thirteenth embodiment directed to any one or more of Aspects 1-4, and also combinable with any one or more of Embodiments 1-12, the buffer solution has a pH ranging from about 8.0 to 10.5.

Embodiment 14

In a fourteenth embodiment directed to Aspect 1, and combinable with any one or more of Embodiments 1-13, one of the first, second or third containers further comprises a bioactive agent.

Embodiment 15

In a fifteenth embodiment directed to Aspect 1, and combinable with any one or more of Embodiments 1-13, the kit comprises a fourth container comprising a bioactive agent.

Embodiment 16

In a sixteenth embodiment directed to Aspect 2, and combinable with any one or more of Embodiments 1-13, the liquid composition further comprises a bioactive agent.

Embodiment 17

In a seventeenth embodiment directed to any one or more of Embodiments 14-16, the bioactive agent is a corticosteroid, e.g., triamcinolone or a pharmaceutically acceptable salt or ester of triamcinolone such as triamcinolone acetonide or triamcinolone hexacetonide.

Embodiment 18

In an eighteenth embodiment directed to Aspect 1, and combinable with any one or more of Embodiments 1-15, 17, the first container comprises from about 0.1 weight % to about 3.5 weight percent of the thiol-functionalized polyethylene glycol relative to the vinyl sulfone-derivatized hyaluronic acid (w/w).

Embodiment 19

In an nineteenth embodiment directed to any one or more of Aspects 1-4, and combinable with any one or more of Embodiments 1-18, the concentration of the thiol-functionalized polyethylene glycol in the final liquid composition ranges from about 10-300 mg/mL, or from about 6-250 mg/mL, or from about 8-200 mg/mL.

Embodiment 20

In a twentieth embodiment directed to Aspect 3, and combinable with any one or more of Embodiments 1-13 and/or 19, a bioactive agent is added to the vinyl sulfone-derivatized hyaluronic acid-thiol-functionalized polyethylene glycol-containing solution of step (i), or to the buffer solution from step (ii) prior to the combining, or to the liquid composition formed in step (ii).

Embodiment 21

In this embodiment directed to Embodiment 20, the bioactive agent is a corticosteroid, e.g., is triamcinolone or a pharmaceutically acceptable salt or ester of triamcinolone such as triamcinolone acetonide or triamcinolone hexacetonide.

Embodiment 22

In this embodiment directed to Aspect 4, and combinable with any one or more of Embodiments 1-13, the portion of thiol-functionalized polyethylene glycol in step (i) comprises from about 0.1 weight % to about 3.5 weight percent thiol-functionalized polyethylene glycol relative to the vinyl sulfone-derivatized hyaluronic acid (w/w).

Embodiment 23

In this embodiment directed to Aspect 4, and combinable with any one or more of Embodiments 1-13 and/or 22, a bioactive agent is added to the solution of step (i), or to the vinyl sulfone-derivatized hyaluronic acid-thiol-functionalized polyethylene glycol-containing solution from step (iii), or to the buffer solution from step (iv) prior to mixing, or to the liquid composition formed in step (iv).

Embodiment 24

In this embodiment related to Embodiment 23, the bioactive agent is a corticosteroid, e.g., is triamcinolone or a pharmaceutically acceptable salt or ester of triamcinolone such as triamcinolone acetonide or triamcinolone hexacetonide.

Embodiment 25

In this embodiment, provided herein is a kit or sprayable liquid composition according to Aspects 1 and/or 2, and combinable with any one or more of Embodiments 1-19, for use in application to a body site.

Embodiment 26

In this embodiment related to Embodiment 25, the kit or sprayable liquid composition may be used for embryonic development, tissue organization, tissue sealing applications, wound healing, angiogenesis, tumorigenesis, for preventing surgical adhesions, or treatment of osteoarthritis or rheumatoid arthritis, for arthroscopic or open joint surgery to repair tissue of the joint (i.e., cartilage), and to effect hemostasis.

EXAMPLES

The following examples are put forth to provide those of ordinary skill in the art with a complete disclosure and description of how the compounds, compositions, and methods provided herein are made and evaluated, and are intended to be purely exemplary. Thus, the examples are in no way intended to limit the scope of what the inventors regard as their invention. There are numerous variations and combinations of reaction conditions, e.g., component concentrations, desired solvents, solvent mixtures, temperatures, pressures, and other reaction parameters and conditions that may be employed to optimize product characteristics such as purity, yield, and the like. Such are considered as well within the scope of the present disclosure. Any combination of the above-described elements in all possible variations thereof is encompassed by the invention unless otherwise indicated herein or otherwise clearly contradicted by context.

Materials $^1$H NMR Spectrometer: 400 MHz

Polyethylene glycol dithiol, HS—$(CH_2CH_2O)_n$ $CH_2CH_2SH$, "PEG-$(SH)_2$", MW=3350

PEG$(SH)_4$=C$((CH_2O(CH_2CH_2O)_nCH_2CH_2SH)_4$, MW=10,000, pentaerythritol core (Sunbio PEG-SHOP)

Example 1

Synthesis of Vinyl Sulfone Derivatized Hyaluronic Acid (HA-VS)

Mw=100K

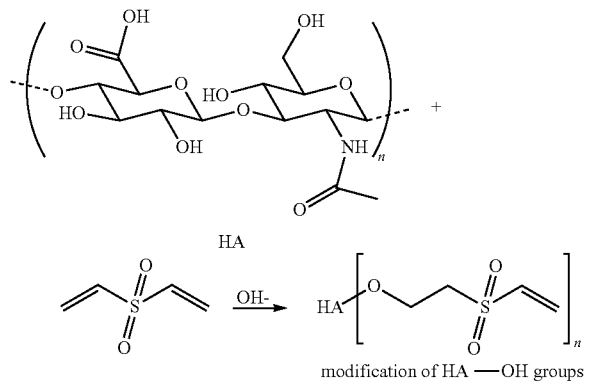

5 g hyaluronic acid (HA) [Mw=100K, Shesiedo] was weighed into a 1 L beaker. 500 mL sterile filtered water was added to the HA. An overhead stirrer with an anchor shaped paddle was used to stir the mixture for 16.5 hrs at which point the HA was dissolved. 333 mL of a 0.25 N NaOH solution (13.9 mL 6N NaOH added to 319 mL deionized water) was added to the stirring HA solution. After about 1 min, 150 mL of a divinyl sulfone solution (18 mL divinyl sulfone dissolved in 132 mL deionized water) was added rapidly to the stirring solution. After 2 minutes (measured from the completion of the divinyl sulfone solution addition), the pH of the solution was adjusted to between 5 and 6 by rapidly adding 13.7 mL 6N HCl. The reaction solution was then dialysed using a tangential flow filtration system (spectrapor system, cartridge P/N M6-100S-301-01P). The total volume was 11 times the original solution volume. Once the purification step was completed, the solution was concentrated to approximately 400 mL. The vinyl sulfone functionalized HA (HA-VS) was removed from the TFF system and was placed in a glass container which was then frozen using dry ice/acetone. The material was then lyophilized. Once dried, the material (4.6 g) was placed in a foil pouch and heat sealed. A sample of the modified HA was sent for $^1$H-NMR analysis.

Figure 2:
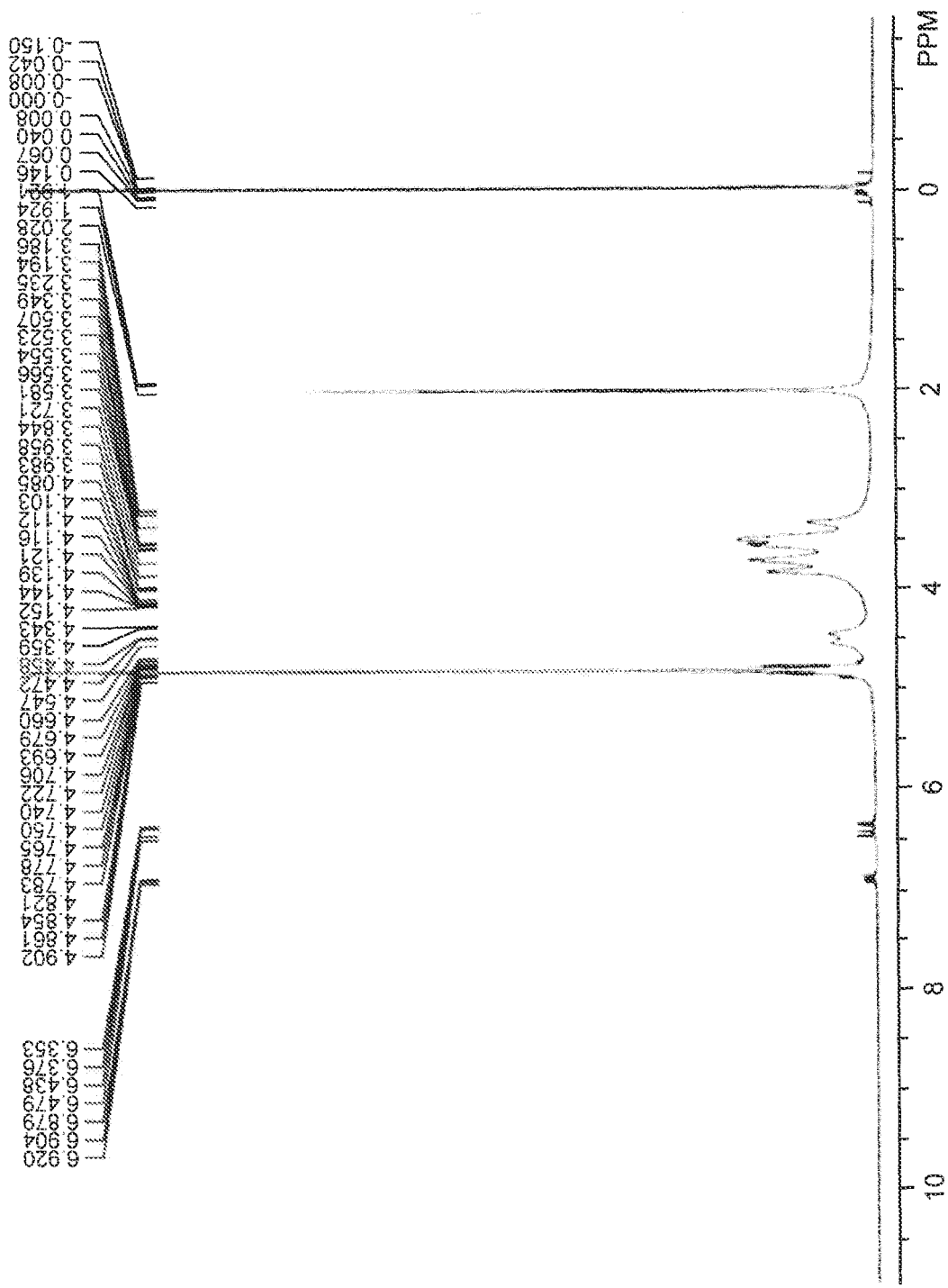
FIG. 2 is a $^1$H NMR spectrum of vinyl-sulfone modified hyaluronic acid (HA-VS) prepared as described in Example 1 (in $D_2O$). Based upon the NMR, the hyaluronic acid was determined to possess a level of vinyl sulfone substitution of approximately 11% per disaccharide.

The $^1$H-NMR spectrum (FIG. 2) showed that the HA had a vinyl sulfone substitution level of approximately 11%.

Example 2

Synthesis of Vinyl Sulfone Derivatized Hyaluronic Acid (HA-VS)

IV=1.3 m$^3$/kg 20 g hyaluronic acid (HA) [Intrinsic viscosity (IV) 1.3 m$^3$/kg, Shesiedo] was weighed into a 4 L beaker. 2000 mL sterile filtered water was added to the HA. An overhead stirrer with an anchor shaped paddle was used to stir the mixture for 16.5 hrs at which point the HA was dissolved. 1335 mL of a 0.25 N NaOH solution (55.6 mL 6N NaOH added to 1280 mL deionized water) was added to the stirring HA solution. After about 1 min, a divinyl sulfone solution (72 mL divinyl sulfone dissolved in 530 mL deionized water) was added rapidly to the stirring solution. After 2 minutes (measured from the completion of the divinyl sulfone solution addition), the pH of the solution was adjusted to between 5 and 6 by rapidly adding 55 mL 6N HCl. The reaction solution was then dialysed using a tangential flow filtration system (spectrapor system, cartridge P/N M6-100S-301-01P). The total volume was 11 times the original solution volume. Once the purification step was completed, the solution was concentrated to approx 2600 mL. The vinyl sulfone functionalized HA (HA-VS) was removed from the TFF system and was placed in stainless steel tray. The material was then lyophilized using a Millrock lyophilizer. Once dried, the material (20.15 g) was placed in foil pouches which were then heat sealed. A sample of the modified HA was sent for $^1$H-NMR analysis.

The $^1$H-NMR spectrum showed that the HA had a vinyl sulfone substitution level of approximately 14%.

Example 3

Synthesis of Vinyl Sulfone Derivatized Hyaluronic Acid (HA-VS)

20 g hyaluronic acid (HA) [Mw=900K, Novozymes] was weighed into a 4 L beaker. 2000 mL sterile filtered water was added to the HA. An overhead stirrer with an anchor shaped paddle was used to stir the mixture for 16.5 hrs at which point the HA was dissolved. 1335 mL of a 0.25 N NaOH solution (55.6 mL 6N NaOH added to 1280 mL deionized water) was added to the stirring HA solution. After about 1 min, a divinyl sulfone solution (72 mL divinyl sulfone dissolved in 528 mL deionized water) was added rapidly to the stirring solution. After 2 minutes (as measured from the completion of the divinyl sulfone solution addition), the pH of the solution was adjusted to between 5 and 6 by rapidly adding 56 mL 6N HCl. The reaction solution was then dialysed using a tangential flow filtration system (spectrapor system, cartridge P/N M6-100S-301-01P). The total volume was 11 times the original solution volume. Once the purification step was completed, the solution was concentrated to approx 2500 mL. The vinyl sulfone functionalized HA (HA-VS) was removed from the TFF system and was placed in stainless steel tray. The material was then lyophilized using a Millrock lyophilizer. Once dried, the material (17.5 g) was placed in foil pouches which were then heat sealed. A sample of the modified HA was sent for $^1$H-NMR analysis.

The $^1$H-NMR spectrum showed that the HA had a vinyl sulfone substitution level of approximately 20%.

Example 4

Gel Formation

Buffer Effects

The pH of 1 mL of 25 mg/mL HA-VS (Example 3) was adjusted to pH 6.5 to pH 9.5 with various amount of sodium phosphate buffer pH 8 or sodium phosphate buffer pH 9.5 in a sample tube. Dry (powder) PEG(SH)$_2$ was added to the HA-VS solution. The solutions were mixed and the time to gel formation was measured by the visual lack of solution flow. The table below summarizes the samples tested.

TABLE 1

| # | BUFFER pH | BUFFER CONC (MM) | PEG(SH)$_2$ (MG) | GELATION (MIN:SEC) |
|---|---|---|---|---|
| 1 | 8 | 38 | 22.0 | 1:40 |
| 2 | 8 | 38 | 26.4 | 1:15 |
| 3 | 8 | 91 | 22.0 | 0:36 |
| 4 | 8 | 91 | 26.4 | 0:40 |
| 5 | 8.5 | 91 | 26.4 | 0:21 |
| 6 | 9.5 | 91 | 26.4 | instant |

Example 5

Burst Pressure Test

Figure 3:
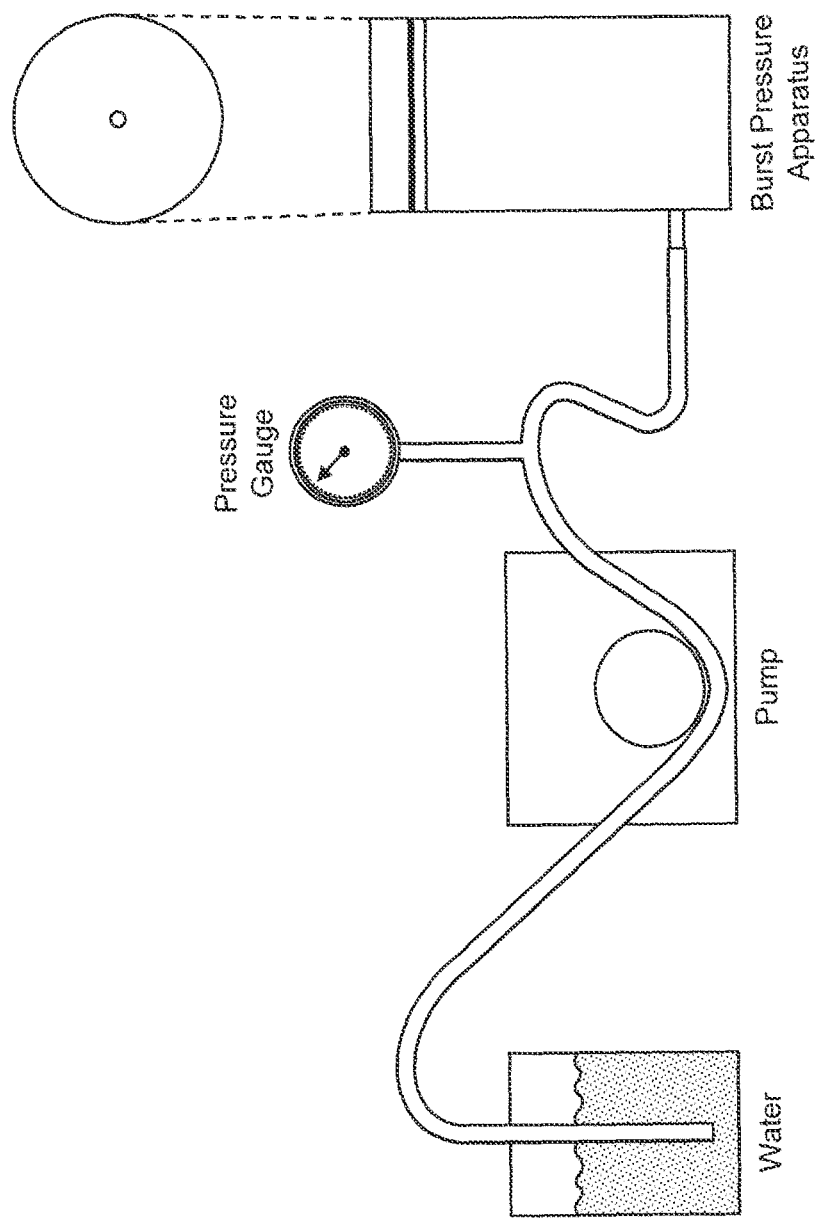
FIG. 3 demonstrates a burst pressure apparatus used to determine burst pressure as described in Example 5.

Burst pressure tests were performed using the setup shown in FIG. 3.

To simulate tissue, collagen sausage casing was used. The sausage casing was placed over the top of the burst pressure apparatus and held in place using a rubber O-ring. A hole was made in the sausage casing using a 18 gauge needle. The in-situ gelling material was placed on the top of the casing is such a manner that the hole (made with the 18 gauge needle) was covered with material. After 5 minutes, the gauge (Omega Model: DPG5500B-05G) was zeroed and the pump was turned on to a flow rate of 100 mL/min. The burst pressure was measured as the maximal pressure on the pressure gauge just prior to water readily flowing through the formed gel.

Example 6

HA-VS/HS-PEG-SH Gelation (HA-VS Substitution 14%)

125 mg of HA-VS (Example 2) was weighed in a 10 mL syringe. The HA-VS was dissolved by adding 5 mL H$_2$O into the syringe and mixed overnight on a rotator. 2.5 mL of dissolved HA-VS was transferred to a new 10 mL syringe. This 10 mL syringe was then autoclaved at 250° F. for 15 min. 40 mg PEG(SH)$_2$ was weighed into a 10 mL syringe. A second aliquot of 40 mg PEG(SH)$_2$ was weighed into a second 10 mL syringe. Gelation was performed with 1.5 mL of both non-autoclaved and autoclaved HA-VS using the following procedure. The syringe containing the HA-VS was connected to the syringe containing the PEG(SH)$_2$ using a luer connector. The HA-VS was transferred to the PEG(SH)$_2$ syringe by pushing the plunger. The contents of the syringes were passed back and forth several times until the PEG(SH)$_2$ has dissolved. 100 ul of 1M sodium phosphate, pH 8.5. buffer was added to the mixture. Gelation time for both conditions was approximately 30 seconds.

Example 7

Gelation Using Di- and Tetra-Functionalized PEGs 150 mg of HA-VS (Example 2) was weighed in a 10 mL syringe. The HA-VS was dissolved by adding 6 mL H$_2$O into the syringe and mixing overnight on a rotator. Gelation was performed with 1.5 mL of HA-VS and either 40 mg PEG(SH)$_2$, or 40 mg PEG(SH)$_4$. 100 μl of 1M sodium phosphate, pH 8.5 buffer was added to each sample to complete gelation. Each solution was applied to sausage casing for Burst pressure testing (Example 5). Each product had gelled by 1 minutes. Burst force was measured.

TABLE 2

| PEG USED | BURST PRESSURE (PSI) |
|---|---|
| PEG(SH)$_2$ | 0.571 |
| PEG(SH)$_2$ | 0.465 |
| PEG(SH)$_2$ | 0.685 |
| PEG(SH)$_4$ | 0.490 |
| PEG(SH)$_4$ | 0.450 |
| PEG(SH)$_4$ | 0.603 |

Example 8

Gelation of E-Beam Sterilized HA-VS 0.4 g of ascorbic acid and 0.4 g of PEG 4000 were dissolved in 50 mL H$_2$O. The solution was adjusted to pH 6.14 using 6N NaOH followed by transferring the solution to 1.25 g of lyophilized HA-VS (Example 2). After mixing thoroughly, 3 mL aliquots were transferred to a Teflon sponge mold, and lyophilized to formed sponges. The sponges were placed in 5 mL syringes and sent for ebeam sterilization at 46 kGy. Gelation was performed by dissolving ½ the sterilized sponge in a PEG(SH)$_2$ (40 mg in 750 ul H$_2$O) solution. 750 ul of 150 mM sodium phosphate, pH 8.4, was added to the HA-VS/PEG(SH)$_2$ solution. The resulted HA-VS concentration was 25 mg/mL. The time to gelation was then measured. Gelation time for non-ebeamed sponge was 52 seconds, and 4 minutes for the e-beamed sponge. Gelation time decreased from 4 minutes to 50 seconds when ebeamed HA-VS concentration increased to 60 mg/mL.

Example 9

Gelation 1

HA-VS (Example 1) was weighed into a 10 mL syringe and was dissolved in H$_2$O to form a 41 mg/mL solution. 40 mg PEG(SH)$_2$ was added to 1.5 mL of the HA-VS solution.

The HA-VS and the PEG(SH)$_2$ were mixed. Once the PEG(SH)$_2$ had dissolved, 100 μl 1M sodium phosphate, pH 8.5, was added and mixed into the mixture. A clear gel was formed within 5 minutes.

Example 10

Gelation 2

HA-VS (Example 1) was weighed into a 1 mL syringe and was dissolved in H$_2$O to form a 60 mg/mL solution. 10 mg PEG(SH)$_2$ was added to 0.2 mL of the HA-VS solution. The HA-VS and the PEG(SH)$_2$ were mixed. Once the PEG(SH)$_2$ had dissolved, 15 μl 1M sodium phosphate, pH 8.5. was added and mixed into the mixture. The mixture gelled in 40 seconds.

Example 11

Gelation 3

HA-VS (Example 1) was weighed into a 1 mL syringe and was dissolved in H$_2$O to form a 60 mg/mL solution. 10 mg PEG(SH)$_2$ was added to 0.4 mL of the HA-VS solution. The HA-VS and the PEG(SH)$_2$ were mixed. Once the PEG(SH)$_2$ had dissolved, 26.7 μl 1M sodium phosphate, pH 8.5. was added and mixed into the mixture. The mixture gelled in 1 minute 30 seconds.

Example 12

Gelation 4

HA-VS (Example 1) was weighed into a 3 mL syringe and was dissolved in H$_2$O to form a 60 mg/mL solution. 75 mg PEG(SH)$_2$ was added to 1.5 mL of the HA-VS solution. The HA-VS and the PEG(SH)$_2$ were mixed. Once the PEG(SH)$_2$ had dissolved, 115 μl 1M sodium phosphate, pH 8.5. was added and mixed into the mixture. The mixture was then extruded onto the sausage casing (Example 5). The mixture gelled within 2 minutes and the burst pressure (example 5) was measured as 1.24 PSI.

Example 13

Gelation 5

HA-VS (Example 1) was weighed into a 3 mL syringe and was dissolved in H$_2$O to form a 120 mg/mL solution. 75 mg PEG(SH)$_2$ was added to 0.75 mL of the HA-VS solution. The HA-VS and the PEG(SH)$_2$ were mixed. Once the PEG(SH)$_2$ had dissolved, 750 μl 150 mM sodium phosphate, pH 8.8. was added and mixed into the mixture. The mixture gelled in 1 minute 40 seconds.

Example 14

Gelation 6

HA-VS (Example 1) was weighed into a 3 mL syringe and was dissolved in H$_2$O to form a 120 mg/mL solution. 75 mg PEG(SH)$_2$ was added to 0.75 mL of the HA-VS solution. The HA-VS and the PEG(SH)$_2$ were mixed. Once the PEG(SH)$_2$ had dissolved, 750 μl 300 mM sodium phosphate, pH 8.8. was added and mixed into the mixture. The mixture gelled in 40 seconds. The molecular weight of the HA-VS was measured at 100 kDa by GPC.

TABLE 3

| EXAMPLE | HA-VS, % SUBSTITUTION | HA-VS | AMT HA-VS USED IN RXN | PEG-SH$_2$ MG | BUFFER, PH | GEL TIME |
| --- | --- | --- | --- | --- | --- | --- |
| 9 | 11% | 41 mg/mL | 1.5 mL or 61.5 mg HA-VS | 40 mg | 100 μmol sodium phosphate, 8.5 | 5 minutes |
| 10 | 11% | 60 mg/mL | 0.20 mL or 12 mg HA-VS | 10 mg | 15 μmol sodium phosphate, 8.5 | 40 seconds |
| 11 | 11% | 60 mg/mL | 0.40 mL or 24 mg HA-VS | 10 mg | 26.7 μmol sodium phosphate, 8.5 | 1 min 30 seconds |
| 12 | 11% | 60 mg/mL | 1.5 mL or 90 mg HA-VS | 75 mg | 115 μmol sodium phosphate, 8.5 | 2 minutes |
| 13 | 11% | 120 mg/mL | 0.75 mL or 90 mg HA-VS | 75 mg | 112.5 μmol sodium phosphate, 8.8 | 1 minute 40 seconds |
| 14 | 11% | 120 mg/mL | 0.75 mL or 90 mg HA-VS | 75 mg | 225 μmol sodium phosphate, 8.8 | 40 seconds |

Example 15

Gelation 7

Autoclaved HA-VS

HA-VS (Example 1) was weighed into a 3 mL syringe and was dissolved in H$_2$O to form a 120 mg/mL solution. The solution was then autoclaved at 250° F. for 15 min. Once cooled to room temperature, 75 mg PEG(SH)$_2$ was added to 0.75 mL of the HA-VS solution. The HA-VS and the PEG(SH)$_2$ were mixed. Once the PEG(SH)$_2$ had dissolved, 750 μl 300 mM sodium phosphate, pH 8.8. was added and mixed into the mixture. The mixture gelled in 60 seconds.

The molecular weight of the HA-VS after autoclaving was measured at 76 kDa by GPC.

Example 16

Addition of PEG(SH)$_2$ to HA-VS Prior to Autoclaving

PEG(SH)$_2$ was added to HA-VS (120 mg/mL) (Example 1) at. 0, 0.02, 0.2, 0.4, 0.7, 1.0, 1.3, 2.0, 5.0, and 10 mg per mL of HA-VS. After mixing thoroughly, HA-VS/PEG was autoclaved for 15 min at 250° F. Then gelation was performed with 107 mg PEG(SH)$_2$ per mL of HA-VS using 0.3M sodium phosphate, pH 8.8, and 0.15M sodium carbonate, pH 9.25. The materials gelled by 2 minutes. The gels were subjected for burst force tests.

TABLE 4

| # | AUTOCLAVE | PEG(SH)$_2$ (MG) | GELLED AFTER AUTOCLAVE | MW | BURST PRESSURE (PSI) | BURST PRESSURE (PSI) |
|---|---|---|---|---|---|---|
| Run | | | | | 1 | 2 |
| Buffer | | | | | 0.3M Phos, pH 8.8 | 0.15M Carb, pH 9.25 |
| 1 | − | 0 | − | 100 | 1.35 | — |
| 2 | + | 0 | − | 76 | 0.995 | — |
| 3 | + | 0.02 | − | 76 | 0.85 | — |
| 4 | + | 0.2 | − | 86 | 1.03 | 1.74 |
| 5 | + | 0.4 | − | 87 | 1.89 | 2.39 |
| 6 | + | 0.7 | − | 103 | 1.92 | 1.81 |
| 7 | + | 1.0 | − | 139 | 2.5 | 1.03 |
| 8 | + | 1.3 | − | 121 | — | — |
| 9 | + | 2.0 | + | 414 | — | — |
| 10 | + | 5.0 | + | nd | — | — |
| 11 | + | 10 | + | nd | — | — |

Example 17

Gelation 8

Effect of Buffer 120 mg/mL HA-VS (Example 1) was autoclaved at 250° F. for 15 minutes. Gelation were performed using 0.9/1 ratio (g/g) of HA-VS/PEG(SH)$_2$ with the following buffers: (1) 0.3M sodium phosphate, pH 8.8, (2) 0.2M sodium carbonate, pH 9.25, and (3) 0.3M sodium carbonate, pH 9.4. The solutions gelled within 3 minutes and the burst pressure was measured (Example 5).

TABLE 5

| RUN | BUFFER | BURST PRESSURE (PSI) |
|---|---|---|
| 1 | 0.3M Phos, pH 8.8 | 1.30 |
| 2 | 0.2M Carb, pH 9.3 | 1.90 |
| 3 | 0.3M Carb, pH 9.4 | 2.26 |

Example 18

Gelation 9

Effect of Buffer

Three grams HA-VS (Example 1) were dissolved in 25 mL of H$_2$O to form 120 mg/mL HA-VS solution. 60 µl of 100 mg/mL of PEG(SH)$_2$ was added to 6 mL of 120 mg/mL HA-VS at 1 mg PEG per 120 mg HA-VS ratio. 120 mg/mL HA-VS with and without PEG(SH)$_2$ were autoclaved. Gelation was performed for both gels using 108 mg of PEG(SH)$_2$ with 0.3M sodium phosphate, pH 8.8, and 0.15M sodium carbonate, pH 9.25, and 0.3M sodium carbonate, pH 9.4.

TABLE 6

| RUN | AUTOCLAVE | % PEG (G/L) | BUFFER | GELATION TIME (SEC) |
|---|---|---|---|---|
| 1 | + | 0 | 0.15M Carb, pH 9.3 | 18 |
| 2 | + | 0 | 0.3M Carb, pH 9.4 | 9 |
| 3 | + | 0.1 | 0.3M Phos, pH 8.8 | 50 |

TABLE 6-continued

| RUN | AUTOCLAVE | % PEG (G/L) | BUFFER | GELATION TIME (SEC) |
|---|---|---|---|---|
| 4 | + | 0.1 | 0.15M Carb, pH 9.3 | 14 |
| 5 | + | 0.1 | 0.3M Carb, pH 9.4 | Instant |

Example 19

Gelation 10

Gas Assisted Spraying 120 mg/mL HA-VS (Example 1) with PEG/HA-VS 1 mg/120 mg ratio was autoclaved. HA-VS was aliquoted into a 3 mL syringe and was mixed with PEG(SH)$_2$ as detailed in the table below. A buffer solution was then aliqotted into a second 3 mL syringe as defined in the table below. The HA-VS/PEG(SH)$_2$ syringe and the corresponding buffer syringe were attached to a gas assisted spray device (Fibrijet Part # SA-3652, Micromedics). The gas port of the gas assisted spray device was connected to a CO$_2$ tank via a regulator (Tissomat, Baxter). The outlet pressure of the regulator was set at 20 PSI. The solutions were then sprayed onto a sausage casing by activating the gas supply and depressing the plungers of the HA-VS/PEG(SH)$_2$ syringe and the corresponding buffer syringe simultaneously. The materials gelled on the sausage casing within 1 minute. The adhesiveness of each film to the sausage casing was evaluated by physically touching the film and the adhesiveness of the films was ranked relative to each other with number 1 being weakest and 4 being strongest.

TABLE 7

| RUN | HA-VS (ML) | PEG(SH)$_2$ (MG) | BUFFER (ML) | BUFFER (M) | BUFFER PH | FILM EVEN | ADHESIVE RANK |
|---|---|---|---|---|---|---|---|
| 1 | 1.5 | 160 | 1.5 | 0.15 | 9.25 | Yes | 3 |
| 2 | 1 | 107 | 1 | 0.3 | 8.8 | Yes | 1 |
| 3 | 0.8 | 85.6 | 0.8 | 0.075 | 9.25 | Yes | 2 |
| 4 | 0.8 | 85.6 | 0.8 | 0.3 | 9.4 | yes | 4 |

Example 20

Effect of HA-VS Substitution

Gelation and burst force of HA-VS (Mw approx. 600 kD) with substitution 2%, 6%, 14% (Example 2), and 20% (Example 3) respectively, were conducted. HA-VS was dissolved overnight at 25 mg/mL in deionized H$_2$O in a 3 mL plastic syringe, and then autoclaved (250° F., 15 minutes). 2 mL of each HA-VS solution was mixed with 53 mg of dry PEG(SH)$_2$, and then mixed with 133 µl of 0.3M sodium carbonate, pH 9.4. The mixed material was extruded on sausage casing (Example 5). After 5 minutes, the materials using the 2% substituted HA-VS and the 6% substituted HA-VS had not completely gelled at this time point. The materials using the 14% substituted HA-VS and the 20% substituted HA-VS had gelled by 5 minutes (the materials had gelled within 1 minute). The burst force was measured for the gelled samples.

TABLE 8

| % SUB HA-VS | RUN | BURST PRESSURE (PSI) | AVERAGE (PSI) |
|---|---|---|---|
| 2 | 1 | No gel | Cannot Measure |
|   | 2 | No gel |  |
| 6 | 1 | No gel | Cannot Measure |
|   | 2 | No gel |  |
| 14 | 1 | 3.017 | 2.263 |
|   | 2 | 1.681 |  |
|   | 3 | 2.091 |  |
| 20 | 1 | 2.349 | 1.679 |
|   | 2 | 1.359 |  |
|   | 3 | 1.328 |  |

Example 21

Gas Assisted Spraying 50 mg/mL 14% substituted HA-VS (Example 2) and 20% substituted HA-VS (Example 3) were autoclaved (250° F., 15 minutes) respectively. Each sample was then prepared for gas assisted spraying as follows: The HA-VS was aliquoted into a 3 mL syringe and was mixed with PEG(SH)$_2$ as detailed in the table below. A buffer solution was then aliquoted into a second 3 mL syringe as defined in the table below. The HA-VS/PEG(SH)$_2$ syringe and the corresponding buffer syringe were attached to a gas assisted spray device (Fibrijet Part # SA-3652, Micromedics). The gas port of the gas assisted spray device was connected to a CO$_2$ tank via a regulator (Tissomat, Baxter). The outlet pressure of the regulator was set at 20 PSI. The solutions were then sprayed onto a sausage casing by activating the gas supply and depressing the plungers of the HA-VS/PEG(SH)$_2$ syringe and the corresponding buffer syringe simultaneously. The materials gelled on the sausage casing within 1 minute. The adhesiveness of each film to the sausage casing was evaluated by physically touching the film and the adhesiveness of the films was ranked relative to each other with number 1 being weakest and 2 being strongest.

TABLE 9

| RUN | HA-VS % SUB | PEG(SH)$_2$ (MG) | BUFFER (M) | BUFFER PH | FILM EVEN | ADHESIVE RANK |
|---|---|---|---|---|---|---|
| 1 | 14 | 53 | 0.3 | 9.4 | Yes | 2 |
| 2 | 20 | 53 | 0.3 | 8.4 | Yes | 1 |

It is claimed:

1. A kit comprising components for preparing a rapid-gelling composition, the kit comprising:
   (i) a first container comprising an aqueous solution of vinyl sulfone-derivatized hyaluronic acid ("HA-VS") at a concentration of from about 10-300 mg/mL, where HA-VS is (2-(vinylsulfonyl)ethoxy)hyaluronic acid, and the HA-VS has from about 11-35% of its hydroxyl groups transformed to 2-(vinylsulfonyl)ethoxy groups,
   (ii) a second container comprising a thiol-functionalized polyethylene glycol having from 2 to 8 thiol groups, and
   (iii) a third container comprising a 30-1000 mM buffer solution at a pH ranging from about 8.0-10.5, in an amount effective, when mixed with the contents of the first and second containers, to provide a solution having a HA-VS concentration of 2-8% (w/v) and a thiol-functionalized polyethylene glycol concentration of 2-8% (w/v),
   wherein the components of the first, second and third containers, when combined, are effective to form a gel within about 10 minutes of mixing.

2. A rapid-gelling, liquid composition formed from the combination of
   (i) an aqueous solution of vinyl sulfone-derivatized hyaluronic acid ("HA-VS") at a concentration of from about 10-300 mg/mL, where HA-VS is (2-(vinylsulfonyl)ethoxy)hyaluronic acid, and the HA-VS has from about 11-35% of its hydroxyl groups transformed to 2-(vinylsulfonyl)ethoxy groups, (ii) a thiol-functionalized polyethylene glycol having from 2 to 8 thiol groups, and (iii) a 30-1000 mM buffer solution at a pH ranging from about 8.0-10.5,
where the concentration of the thiol-functionalized polyethylene glycol in the liquid composition ranges from about 4-300 mg/mL, and
the liquid composition is effective to form a gel within from about ten minutes of mixing components (i), (ii) and (iii).

3. The kit of claim 1, wherein the vinyl sulfone-derivatized hyaluronic acid has from about 15-20%, of its hydroxyl groups substituted with vinyl sulfone.

4. The kit of claim 1, wherein the thiol-functionalized polyethylene glycol has a number of thiol groups selected from the group consisting of 2, 3, and 4.

5. The kit of claim 1, wherein the vinyl sulfone-derivatized hyaluronic acid has an average molecular weight ranging from about 20,000 to about 200,000 daltons.

6. The kit of claim 1, wherein the thiol-functionalized polyethylene glycol is linear or branched.

7. The kit of claim 1, wherein the thiol-functionalized polyethylene glycol has an average molecular weight of from about 1,000 to about 10,000 daltons.

8. The kit of claim 1, wherein the molecular weight of the thiol-functionalized polyethylene glycol is less than the molecular weight of the vinyl sulfone-derivatized hyaluronic acid.

9. The kit of claim 1, wherein the aqueous solution of vinyl sulfone-derivatized hyaluronic acid ("HA-VS") has a concentration ranging from about 20-200 mg/mL.

10. The kit of claim 1, wherein the thiol-functionalized polyethylene glycol is in the form of a powder.

11. The kit of claim 1, wherein the amount of thiol-functionalized polyethylene glycol relative to vinyl sulfone-derivatized hyaluronic acid ranges from about 1:1 (w/w) to about 0.4:1 (w/w).

12. The kit of claim 1, wherein either one of the first, second or third containers further comprises a bioactive agent or the kit further comprises a fourth container comprising a bioactive agent.

13. The liquid composition of claim 2, further comprising a bioactive agent.

14. The liquid composition of claim 13, wherein the bioactive agent is a corticosteroid selected from the group consisting of triamcinolone, triamcinolone acetonide or triamcinolone hexacetonide.

15. The kit of claim 12, wherein the bioactive agent is a corticosteroid selected from the group consisting of triamcinolone, triamcinolone acetonide and triamcinolone hexacetonide.

16. The kit of claim 1, wherein the first container further comprises from about 0.1 weight % to about 3.5 weight percent of the thiol-functionalized polyethylene glycol relative to the vinyl sulfone-derivatized hyaluronic acid (w/w).

17. A method of forming a liquid composition capable of rapid in-situ gel formation, comprising:
(i) adding a thiol-functionalized polyethylene glycol having from 2 to 8 thiol groups to a aqueous solution of vinyl sulfone-derivatized hyaluronic acid ("HA-VS") having a concentration of from about 4-300 mg/mL, where HA-VS is (2-(vinylsulfonyl)ethoxy)hyaluronic acid, and the HA-VS has from about 11-35% of its hydroxyl groups transformed to 2-(vinylsulfonyl) ethoxy groups, to thereby dissolve the thiol-functionalized polyethylene glycol to form a vinyl sulfone-derivatized hyaluronic acid-thiol-functionalized polyethylene glycol-containing solution, and (ii) combining the solution from step (i) with a 30-1000 mM buffer solution at a pH ranging from about 8.0-10.5, to thereby form a liquid composition having a HA-VS concentration of 2-8% (w/v) and a thiol-functionalized polyethylene glycol concentration of 2-8% (w/v),
wherein the liquid composition is effective to form a gel within about 10 minutes of combining.

18. The method of claim 17, wherein:
(i) the vinyl sulfone-derivatized hyaluronic acid has an average molecular weight ranging from about 20,000 to about 200,000 daltons; and/or
(ii) the aqueous solution of the vinyl sulfone-derivatized hyaluronic acid ("HA-VS") has a concentration ranging from about 20-200 mg/mL; and/or
(iii) the molecular weight of the thiol-functionalized polyethylene glycol is less than the molecular weight of the vinyl sulfone-derivatized hyaluronic acid; and/or
(iv) the amount of thiol-functionalized polyethylene glycol relative to vinyl sulfone-derivatized hyaluronic acid ranges from about 1:1 (w/w) to about 0.4:1 (w/w).

19. The method of claim 17, further comprising adding a bioactive agent to the vinyl sulfone-derivatized hyaluronic acid-thiol-functionalized polyethylene glycol-containing solution of step (i), or to the buffer solution from step (ii) prior to the combining, or to the liquid composition formed in step (ii).

20. The method of claim 19, wherein the bioactive agent is a corticosteroid selected from the group consisting of triamcinolone, triamcinolone acetonide or triamcinolone hexacetonide.

21. A method of forming a liquid composition capable of rapid, in-situ gel formation, comprising:
(i) adding a portion of an overall amount of thiol-functionalized polyethylene glycol to an aqueous solution of vinyl sulfone-derivatized hyaluronic acid ("HA-VS") having a concentration of from about 10-300 mg/mL, where HA-VS is (2-(vinylsulfonyl)ethoxy)hyaluronic acid, and the HA-VS has from about 11-35% of its hydroxyl groups transformed to 2-(vinylsulfonyl) ethoxy groups, to thereby form a solution,
(ii) optionally sterilizing the solution from step (i),
(iii) adding to the solution from step (i) or step (ii) if carried out, the remaining amount of thiol-functionalized polyethylene glycol, where the thiol-functionalized polyethylene glycol has from 2 to 8 thiol groups, to thereby dissolve the remaining amount of thiol-functionalized polyethylene glycol to form a vinyl sulfone-derivatized hyaluronic acid-thiol-functionalized polyethylene glycol-containing solution, and
(iv) mixing the vinyl sulfone-derivatized hyaluronic acid-thiol-functionalized polyethylene glycol-containing solution with a 30-1000 mM buffer solution at a pH ranging from about 8.0-10.5,
to thereby form a liquid composition having a HA-VS concentration of 2-8% (w/v) and a thiol-functionalized polyethylene glycol concentration of 2-8% (w/v), to thereby form a liquid composition effective to form a gel within about 10 minutes of mixing.

22. The method of claim 21, wherein the portion of thiol-functionalized polyethylene glycol in step (i) comprises from about 0.1 weight % to about 3.5 weight percent thiol-functionalized polyethylene glycol relative to the vinyl sulfone-derivatized hyaluronic acid (w/w).

23. The method of claim 21, further comprising adding a bioactive agent to the solution of step (i), or to the vinyl sulfone-derivatized hyaluronic acid-thiol-functionalized polyethylene glycol-containing solution from step (iii), or to the buffer solution from step (iv) prior to mixing, or to the liquid composition formed in step (iv).

24. The method of claim 23, wherein the bioactive agent is a corticosteroid selected from the group consisting of triamcinolone, triamcinolone acetonide and triamcinolone hexacetonide.

25. A method of for treating a condition selected from the group of osteoarthritis, rheumatoid arthritis, a wound and reduction of surgical adhesions, by applying the liquid composition of claim 2 to a body site in a subject suffering from the condition.

26. The kit of claim 1, wherein one or more of the kit components is sterile.

27. The liquid composition of claim 2, having one or more components in sterile form.

28. The method of claim 21, comprising (ii) sterilizing the solution from step (i) and/or where either one or both of the thiol-functionalized polyethylene glycol from step (iii) and the buffer solution is sterile.

29. A hydrogel formed from the liquid composition of claim 2.

30. A method for repairing tissue of a joint during arthroscopic or open joint surgery by applying the liquid composition of claim 2 to the tissue.

* * * * *